(12) United States Patent
Aoki et al.

(10) Patent No.: US 9,734,361 B2
(45) Date of Patent: Aug. 15, 2017

(54) INFORMATION RECORDING MEDIUM, COLUMNAR BODY HAVING INFORMATION RECORDING MEDIUM AFFIXED THERETO, INFORMATION READING DEVICE THEREFOR, PHARMACEUTICAL INJECTION DEVICE USING THIS INFORMATION READING DEVICE, INFORMATION READING METHOD, AND NON-TRANSITORY COMPUTER READABLE MEDIUM

(71) Applicant: Panasonic Healthcare Holdings Co., Ltd., Minato-ku, Tokyo (JP)

(72) Inventors: Tooru Aoki, Ehime (JP); Seiji Kikuchi, Ehime (JP); Mitsuteru Fujimoto, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 15/371,130

(22) Filed: Dec. 6, 2016

(65) Prior Publication Data

US 2017/0140177 A1    May 18, 2017

Related U.S. Application Data

(62) Division of application No. 14/236,329, filed as application No. PCT/JP2012/004935 on Aug. 2, 2012, now Pat. No. 9,563,790.

(30) Foreign Application Priority Data

Aug. 3, 2011    (JP) .................................. 2011-169853

(51) Int. Cl.
*G06F 17/00*    (2006.01)
*G06K 5/00*    (2006.01)
(Continued)

(52) U.S. Cl.
CPC ................ *G06K 5/00* (2013.01); *A61M 5/31* (2013.01); *G06K 19/06009* (2013.01);
(Continued)

(58) Field of Classification Search
USPC ......................................... 235/375, 437, 494
See application file for complete search history.

(56) References Cited

U.S. PATENT DOCUMENTS 6,234,392 B1    5/2001 Murakami
2006/0243804 A1    11/2006 Christoffersen et al.
(Continued)

FOREIGN PATENT DOCUMENTS

CN    1863495 A    11/2006
CN    101529448 A    9/2009
(Continued)

OTHER PUBLICATIONS

International Search Report of PCT Application No. PCT/JP2012/004935.
(Continued)

*Primary Examiner* — Rafferty Kelly
(74) *Attorney, Agent, or Firm* — Shinjyu Global IP

(57) ABSTRACT

It is an object to provide an information recording medium with which information symbols can be suitably read. This information recording medium comprises a sheet-form member, a plurality of information symbols that are displayed on the surface of the sheet-form member and each have the same information, and an edge line that is provided at one end and/or the other end of the sheet-form member and allows an information reading device which reads the information symbols to recognize the end of the sheet-form member.

6 Claims, 19 Drawing Sheets

(51) Int. Cl.
*G06K 19/06* (2006.01)
*A61M 5/31* (2006.01)
*A61M 5/20* (2006.01)

(52) U.S. Cl.
CPC . *G06K 19/06056* (2013.01); *A61M 2005/206* (2013.01); *A61M 2005/3126* (2013.01); *A61M 2205/6072* (2013.01)

(56) References Cited

U.S. PATENT DOCUMENTS

| | | |
|---|---|---|
| 2008/0121688 A1 | 5/2008 | Harrop |
| 2010/0194537 A1 | 8/2010 | Nielsen et al. |
| 2011/0132778 A1* | 6/2011 | Austera ............... B01L 3/54 205/792 |
| 2012/0211566 A1 | 8/2012 | Hensel et al. |

FOREIGN PATENT DOCUMENTS

| | | |
|---|---|---|
| EP | 1608305 A1 | 12/2005 |
| JP | S63-118894 A | 5/1988 |
| JP | H07-302313 A | 11/1995 |
| JP | H10-083139 A | 3/1998 |
| JP | H10-111906 A | 4/1998 |
| JP | 2004-298550 A | 10/2004 |
| JP | 2010-503076 A | 1/2010 |
| WO | 86/05906 A1 | 10/1986 |
| WO | 2005/032449 A1 | 4/2005 |
| WO | 2008/028028 A2 | 3/2008 |
| WO | WO2009015933 A1 | 2/2009 |
| WO | WO2011033013 A1 | 3/2011 |

OTHER PUBLICATIONS

European Search Report from the corresponding European Patent Application No. 12819315.8 issued on Jul. 27, 2015.
Office Action from the corresponding Chinese Patent Application No. 201280038387.9 issued on Oct. 27, 2015.
The Notice of Allowance from the corresponding Japnese Patent Application No. 2014-230956 issued on May 24, 2016.
Office Action from the corresponding European Patent Application No. 12819315.8 issued on May 12, 2017.

* cited by examiner

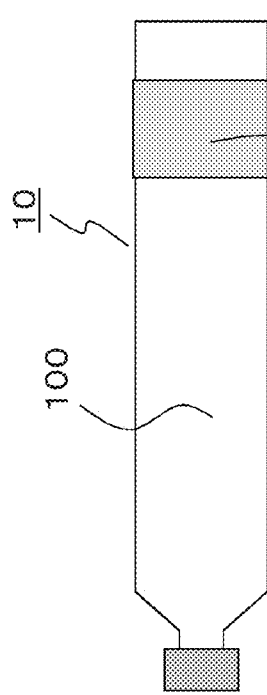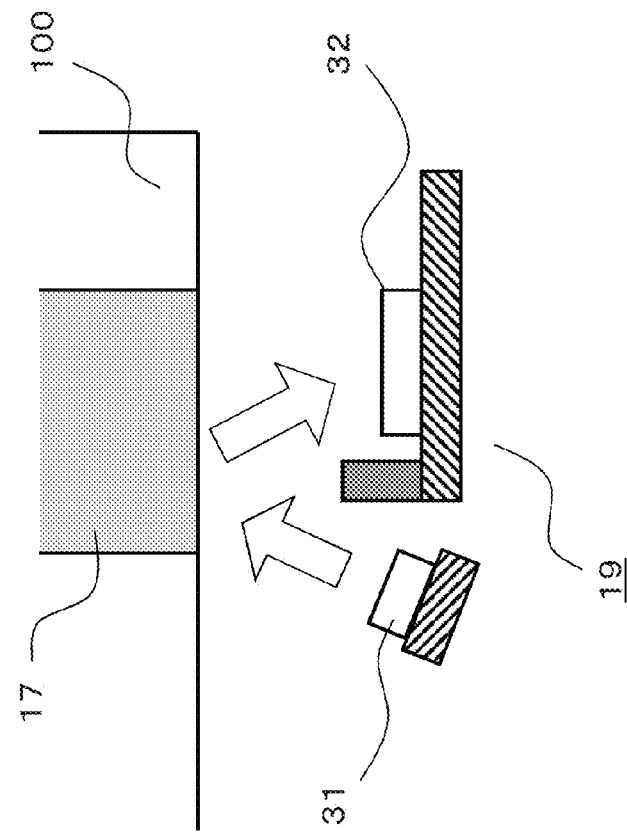
FIG. 5A
FIG. 5B

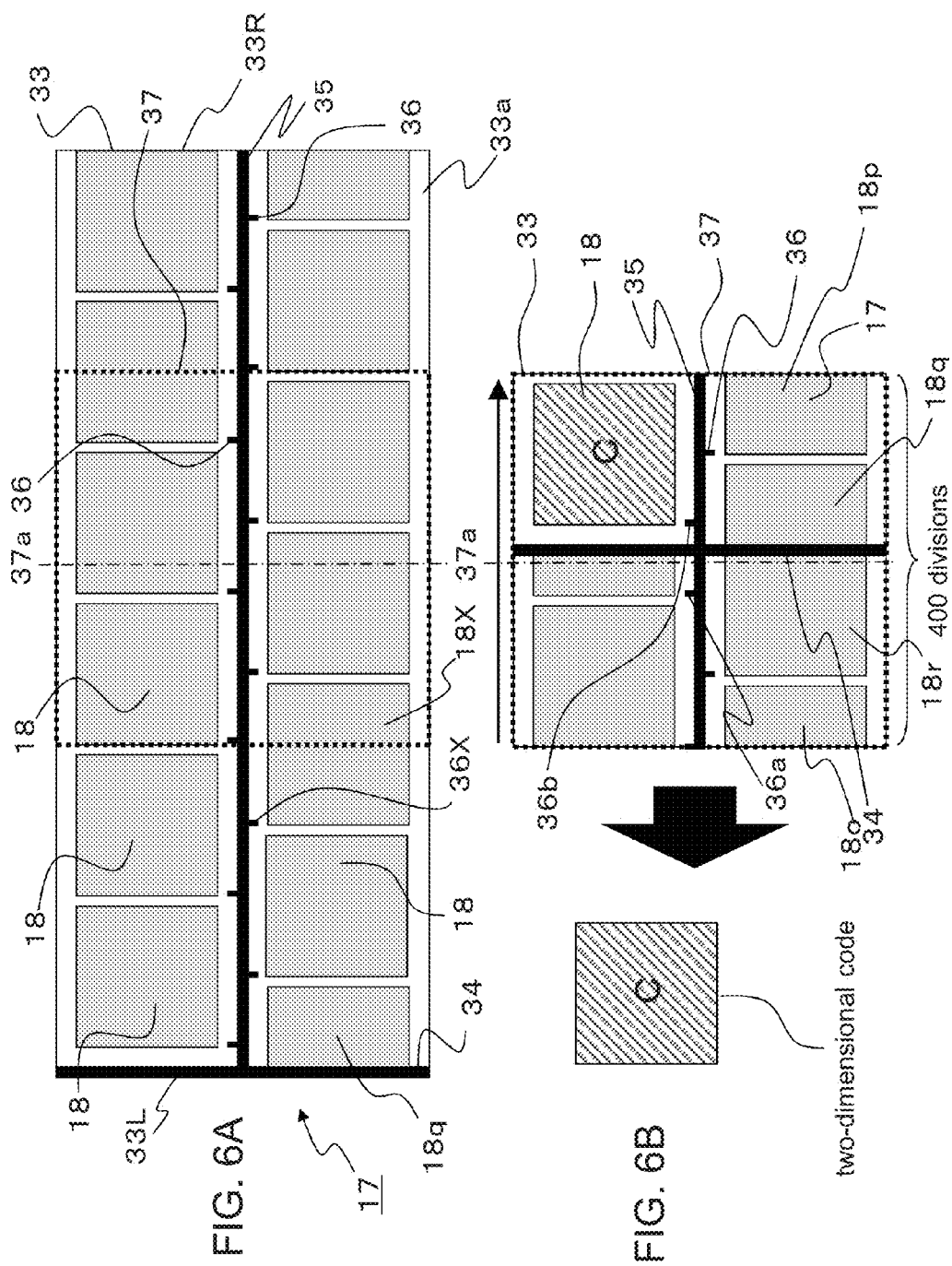

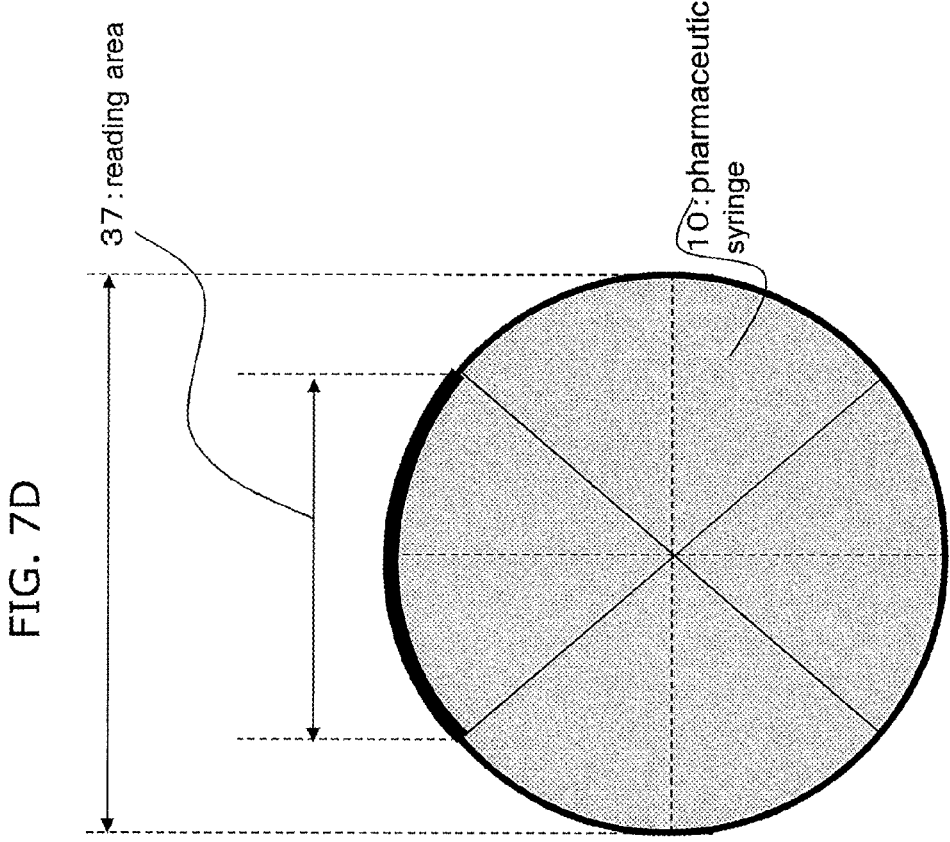
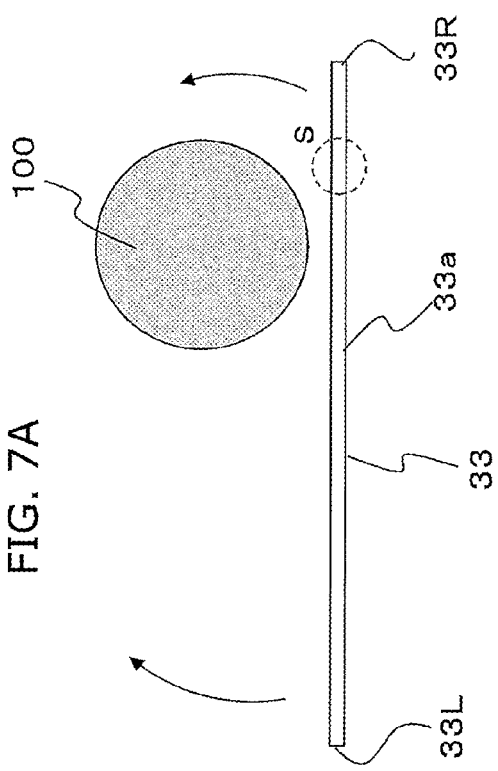
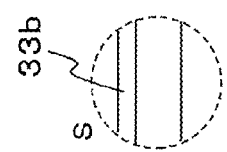
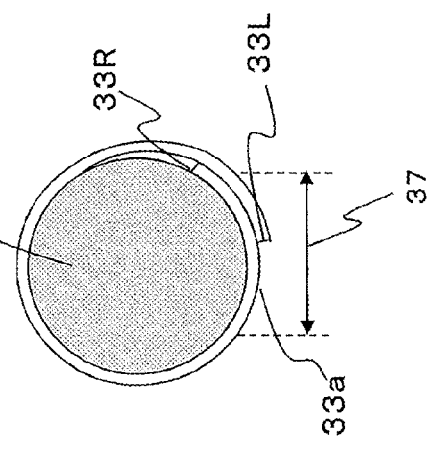

FIG. 13A

| Code | X coordinate of start mark | Code position (0: top row / 1: bottom row) |
|---|---|---|
| B1 | 162 | 0 |
| C1 | 238 | 0 |
| E1 | 76 | 1 |
| G1 | 314 | 1 |

| Code | Distance from center |
|---|---|
| B1 | 0 |
| C1 | 38 |
| E1 | 86 |
| G1 | 114 |

| Code | X coordinate of start mark | Code position (0: top row / 1: bottom row) |
|---|---|---|
| E2 | 114 | 1 |
| C2 | 276 | 0 |
| A2 | 43 | 0 |
| G2 | 351 | 1 |

FIG. 14

| Code | X coordinate of start mark | Code position (0: top row / 1: bottom row) |
|---|---|---|
| A4 | 114 | 0 |
| F4 | 265 | 1 |
| D4 | 27 | 1 |
| C4 | 351 | 0 |

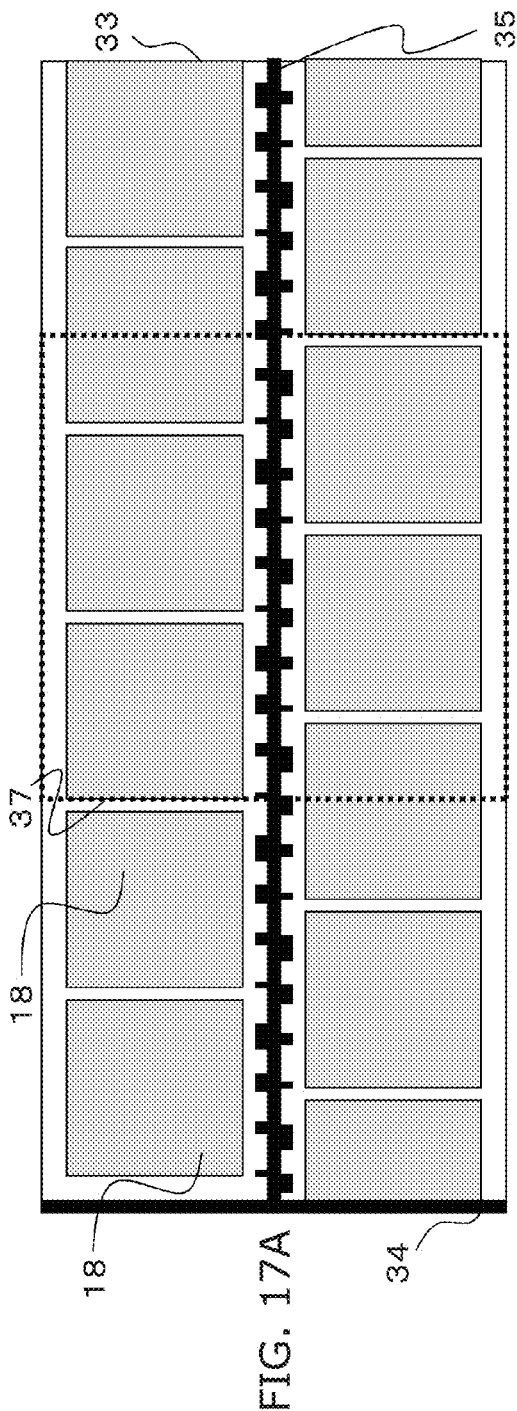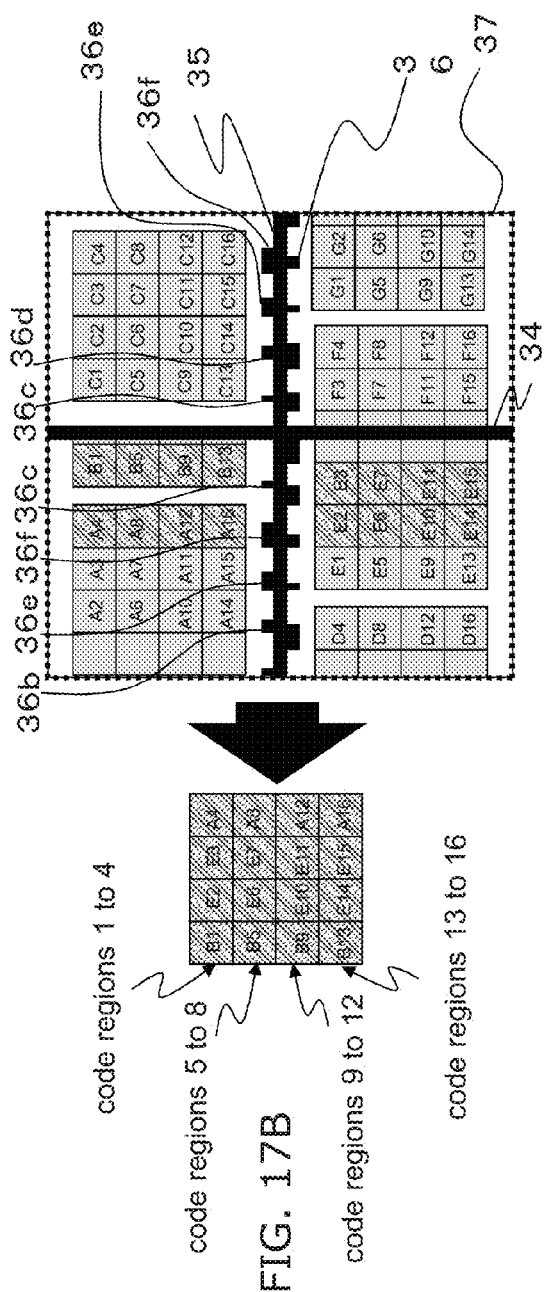

INFORMATION RECORDING MEDIUM, COLUMNAR BODY HAVING INFORMATION RECORDING MEDIUM AFFIXED THERETO, INFORMATION READING DEVICE THEREFOR, PHARMACEUTICAL INJECTION DEVICE USING THIS INFORMATION READING DEVICE, INFORMATION READING METHOD, AND NON-TRANSITORY COMPUTER READABLE MEDIUM

PRIORITY

This application is a divisional application of U.S. application Ser. No. 14/236,329, filed on Jan. 30, 2014 and claims priority to Japanese Patent Application No. 2011-169853 filed on Aug. 3, 2011 and PCT Application PCT/JP2012/004935 filed on Aug. 2, 2012. The entire disclosures of U.S. application Ser. No. 14/236,329, Japanese Patent Application No. 2011-169853 and PCT Application PCT/JP2012/004935 are hereby incorporated herein by reference.

TECHNICAL FIELD

The present invention relates to an information recording medium for recording types of pharmaceutical, the expiration date, and so forth, as well as a columnar body to which this medium is affixed, an information reading device used for the same, and a pharmaceutical injection device that makes use of this information reading device.

BACKGROUND

A conventional information recording medium of this type comprised a slender sheet-form member and a plurality of identical information symbols displayed on the surface of this sheet-form member (see Japanese Laid-Open Patent Application H10-111906, for example).

If an information symbol becomes soiled or is too far from the light receiving element, the information of that information symbol cannot be read, so reading reliability is enhanced by providing a plurality of the same information symbols.

SUMMARY

Technical Problem

A problem encountered with a conventional information recording medium was that the information could not be read properly when the medium was affixed to the outer peripheral face of a columnar body. Specifically, when the information recording medium was affixed to the outer peripheral face of a columnar body, sometimes there was no information symbol all the way around the outer peripheral face of the columnar body, in which case the information symbol of the information recording medium could not be read by the light receiving element.

Also, if the information recording medium main body that constituted the information recording medium was made in the form of a strip, and this was wound and affixed all the way around the outer peripheral face of the columnar body so that the information symbol would be present all the way around, since the two ends of the sheet-form member overlapped, part of the information symbol would be covered up by the overlapping end of the sheet-form member, and once again the information symbol could not be read by the light receiving element.

In view of this, and in light of the problems encountered with conventional information recording media, it is an object of the present invention to provide an information recording medium, a columnar body, an information reading device, and a pharmaceutical injection device with which information symbols can be properly read.

Solution to Problem

To achieve the stated object, the information recording medium of the present invention comprises a sheet-form member, a plurality of information symbols that are displayed on the surface of the sheet-form member and that each have the same information, and an end recognition component that is provided at one end and/or the other end of the sheet-form member, for allowing an information reading device that reads the information symbols to recognize the end of the sheet-form member. This achieves the desired object.

Advantageous Effects

The present invention provides an information recording medium, a columnar body, an information reading device, and a pharmaceutical injection device with which information symbols can be properly read.

BRIEF DESCRIPTION OF THE DRAWINGS

FIG. 5A is a plan view of a pharmaceutical syringe of the pharmaceutical injection device in Embodiment 1 pertaining to the present invention, and FIG. 5B is a detail view of the pharmaceutical syringe of the pharmaceutical injection device in Embodiment 1 pertaining to the present invention;

FIG. 6A is a plan view of the information recording medium in Embodiment 1 pertaining to the present invention, and FIG. 6B is a front view of the state when the information recording medium has been affixed to a pharmaceutical syringe in Embodiment 1 pertaining to the present invention;

FIG. 7A is a cross section of the pharmaceutical syringe in Embodiment 1 pertaining to the present invention, FIG. 7B is a simplified diagram illustrating the operation of affixing the information recording medium to the pharmaceutical syringe in Embodiment 1 pertaining to the present invention, FIG. 7C is a detail view of the S portion in FIG. 7B, and FIG. 7D is a simplified diagram illustrating the operation of affixing the information recording medium to the pharmaceutical syringe in Embodiment 1 pertaining to the present invention;

FIG. 13A shows a database of the information reading device in Embodiment 2 pertaining to the present invention, and FIG. 13B shows the distance of each code region from the center of the reading area;

FIG. 14 shows a database of the information reading device in Embodiment 2 pertaining to the present invention;

FIG. 17A is a plan view of the information recording medium in Embodiment 3 pertaining to the present invention, and FIG. 17B is a front view of the state when the information recording medium has been affixed to the pharmaceutical syringe in Embodiment 1 pertaining to the present invention;

DETAILED DESCRIPTION

Embodiments of the present invention will now be described through reference to the drawings. It will be apparent to those skilled in the art from this disclosure that the following descriptions of the embodiments are provided for illustration only and not for the purpose of limiting the invention as defined by the appended claims and their equivalents.

Embodiment 1

External Configuration of Pharmaceutical Injection Device

Figure 1:
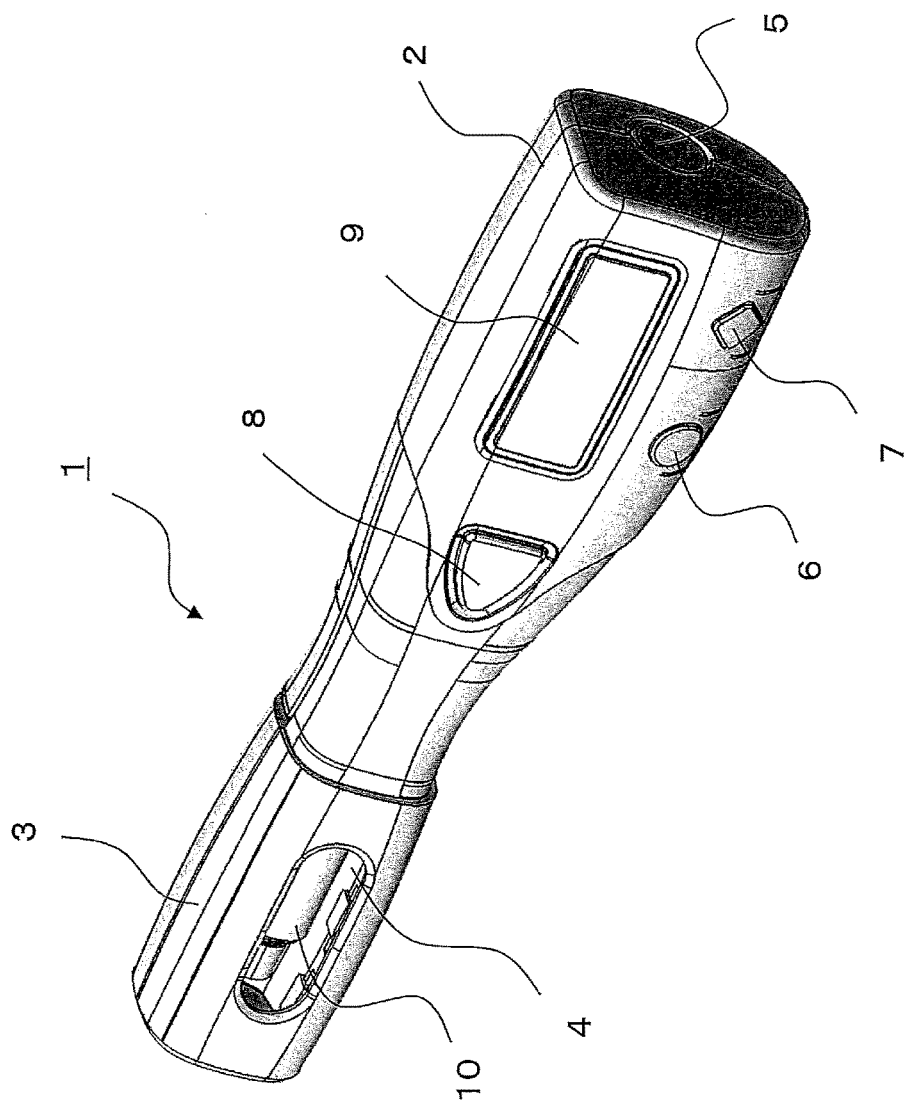
FIG. 1 is an oblique view of a pharmaceutical injection device in Embodiment 1 pertaining to the present invention.
Figure 2:
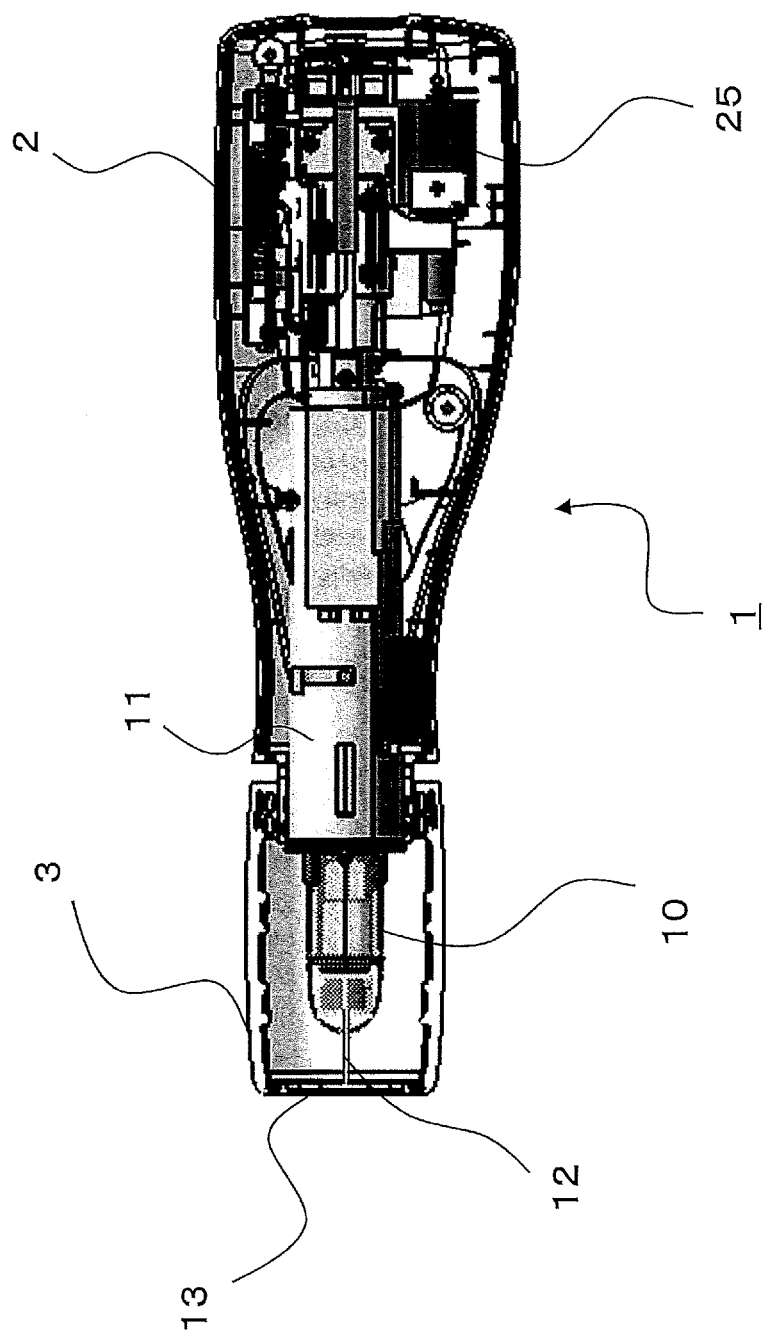
FIG. 2 is a cut-away plan view illustrating the internal configuration of the pharmaceutical injection device in Embodiment 1 pertaining to the present invention.

First, the external configuration of the pharmaceutical injection device in this embodiment will be described. In FIGS. 1 and 2, 1 is a pharmaceutical injection device. This pharmaceutical injection device 1 comprises a substantially cuboid housing 2 that is held in the hand, and a distal end cap 3 attached on the distal end side of this housing 2.

An elliptical check window 4 is provided to the outer peripheral face of the distal end cap 3. A power button 5, an air vent button 6, an end button 7, a pharmaceutical injection button 8, and a display unit 9 are provided on the outer peripheral face of the housing 2.

FIG. 1 shows a state in which a pharmaceutical syringe 10 has been attached to the pharmaceutical injection device 1. This state can be confirmed by visually checking the pharmaceutical syringe 10 through the check window 4.

The distal end cap 3 can be removably attached to the distal end of the housing 2. As shown in FIG. 2, this distal end cap 3 is removed from the distal end of the housing 2 when the pharmaceutical syringe 10 is to be mounted inside an inner case 11 provided inside the housing 2, when it is to be removed from the inner case 11, and when mounting or removing an injection needle 12 for injecting pharmaceutical into the pharmaceutical syringe 10.

As shown in FIG. 1, the distal end cap 3 has the check window 4 for checking the interior as mentioned above, which allows for visual confirmation of whether or not there is a pharmaceutical syringe 10, what type it is, the remaining amount of pharmaceutical, and so on.

As shown in FIG. 2, the distal end cap 3 serves as a cover so that the distal end of the injection needle 12 used for injecting pharmaceutical will not be exposed from the distal end cap 3.

During pharmaceutical injection, the distal end face of this distal end cap 3 is placed against the skin. The injection needle 12 for injecting pharmaceutical is then made to protrude toward the skin from a distal end opening 13 provided to the front face of the distal end cap 3. The injection needle 12 punctures the skin in this state, and the pharmaceutical inside the pharmaceutical syringe 10 is injected into the body.

That is, the distal end cap 3 is provided in order to cover the sharp distal end of the injection needle 12, etc., so that the device is safe to use.

As discussed above, the check window 4 shown in FIG. 1 is a window used for an interior check, by which visual confirmation of whether or not there is a pharmaceutical syringe 10 mounted inside the distal end cap 3, what type of syringe it is, the remaining amount of pharmaceutical, and so on can be performed.

The power button 5 shown in FIG. 1 is provided at the end of the housing 2, and is used to switch power on and off to the pharmaceutical injection device 1.

The air vent button 6 is used to bleed off air from inside the pharmaceutical syringe 10. That is, before the pharmaceutical in the pharmaceutical syringe 10 is injected, there may be air inside the pharmaceutical syringe 10 or inside the injection needle 12 used for injection (a hollow needle in which the inside is a cavity). If this happens, the air vent button 6 is operated to drive the piston drive motor 14 shown in FIG. 3, which is used as an example of an injection driver, and a piston unit 15 pushes the air out of the pharmaceutical syringe 10 and the injection needle 12 to the outside.

Let us go back to FIGS. 1 and 2. The end button 7 is used to move the control processing to the next step after air venting has been performed with the air vent button 6 or after the display on the display unit 9 has been checked, etc.

The pharmaceutical injection button 8 is pressed to inject pharmaceutical once preparation for injecting the pharmaceutical is complete. As discussed above, when the pharmaceutical injection button 8 is pressed, the injection needle 12 punctures the skin, and the pharmaceutical in the pharmaceutical syringe 10 is injected into the body.

The display unit 9 is used to display various kinds of required information, such as the pharmaceutical dosage, the remaining charge of the rechargeable battery installed in the interior (see 16 in FIG. 4), the air venting operation, and so forth, and is constituted by an LCD or an organic EL element.

Internal Structure of the Pharmaceutical Injection Device

Next, internal structure of the pharmaceutical injection device 1 in this embodiment will be described through reference to FIGS. 2 and 3.

Figure 3:
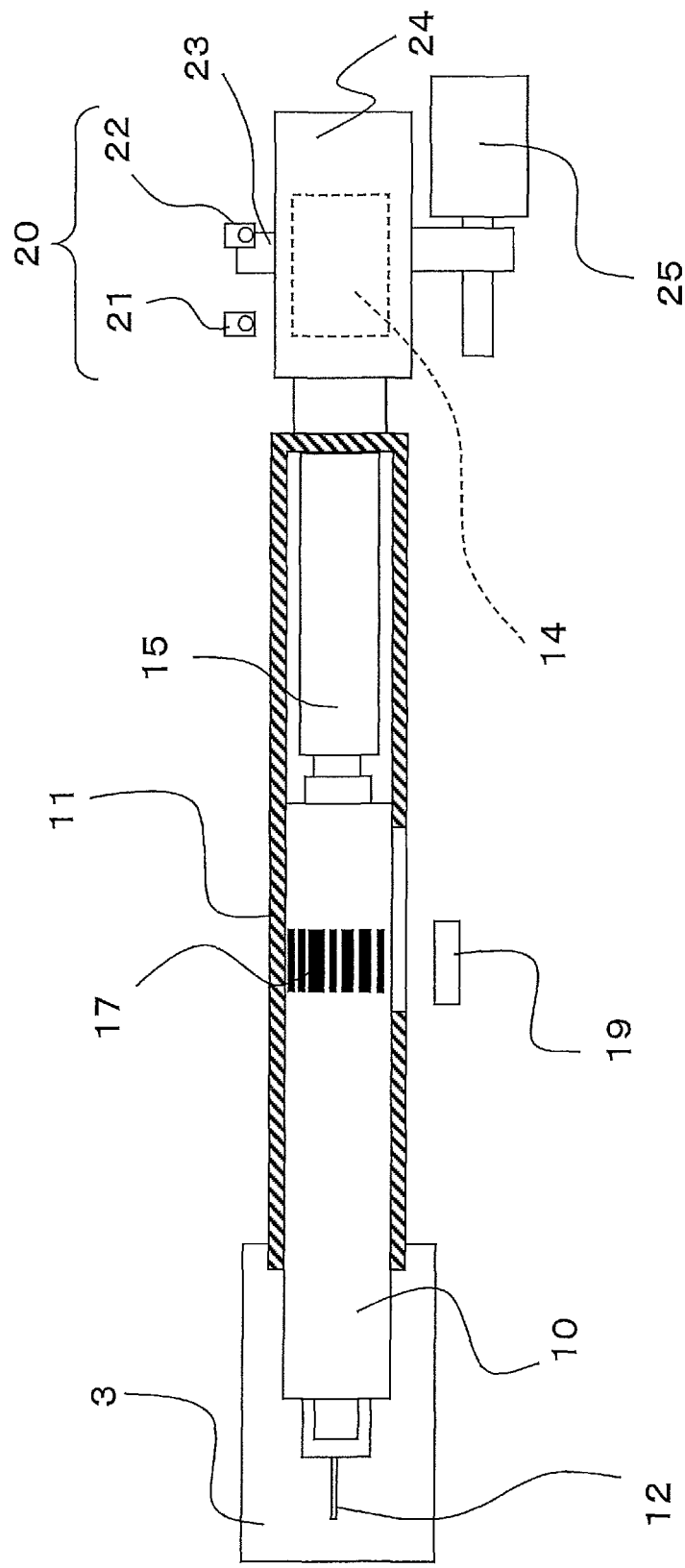
FIG. 3 is a cut-away plan view illustrating the internal configuration of the pharmaceutical injection device in Embodiment 1 pertaining to the present invention.

As shown in FIGS. 2 and 3, the inner case 11, which is a mounting unit of the pharmaceutical syringe 10, is provided inside the housing 2, and the configuration is such that the pharmaceutical syringe 10 is mounted inside this inner case 11 as mentioned above.

The inner case 11 is configured to be able to slide in the longitudinal direction within the housing 2 and within the distal end cap 3 (to the left and right in FIG. 3). The piston unit 15 is housed at the rear of the interior of the inner case 11, and is able to push out the pharmaceutical in the pharmaceutical syringe 10 forward.

The position of the pharmaceutical syringe 10 is restricted with respect to the inner case 11 (removably fixed during mounting). As shown in FIGS. 5A and 5B, an information symbol 18 (discussed below) on the information recording medium 17 affixed to the outer peripheral face at the rear part (to the right in FIGS. 5A and 5B) of the pharmaceutical syringe 10 is read by the information reading device 19 shown in FIG. 3. The information recording medium 17 and the information reading device 19 will be described in detail below.

Next, the position detecting means 20 shown in FIG. 3 is constituted by disposing transmission- or reflection-type photosensors 21 and 22 at two locations a specific distance apart.

Of these, the photosensor 21 detects that the inner case 11 is in the puncture position. The photosensor 22 detects that the inner case 11 is in the retracted position.

23 is a barrier, and the position of the inner case 11 is detected by blocking or transmitting light from or to the photosensors 21 and 22 when the barrier 23 slides in the longitudinal direction. The barrier 23 is formed integrally with a case 24 that houses the piston drive motor 14. This case 24 is linked to the inner case 11 and a slide motor 25, so when the slide motor 25 rotates, the case 24 slides in the longitudinal direction.

Control Configuration of Pharmaceutical Injection Device

The control blocks of the pharmaceutical injection device 1 in this embodiment will now be described.

Figure 4:
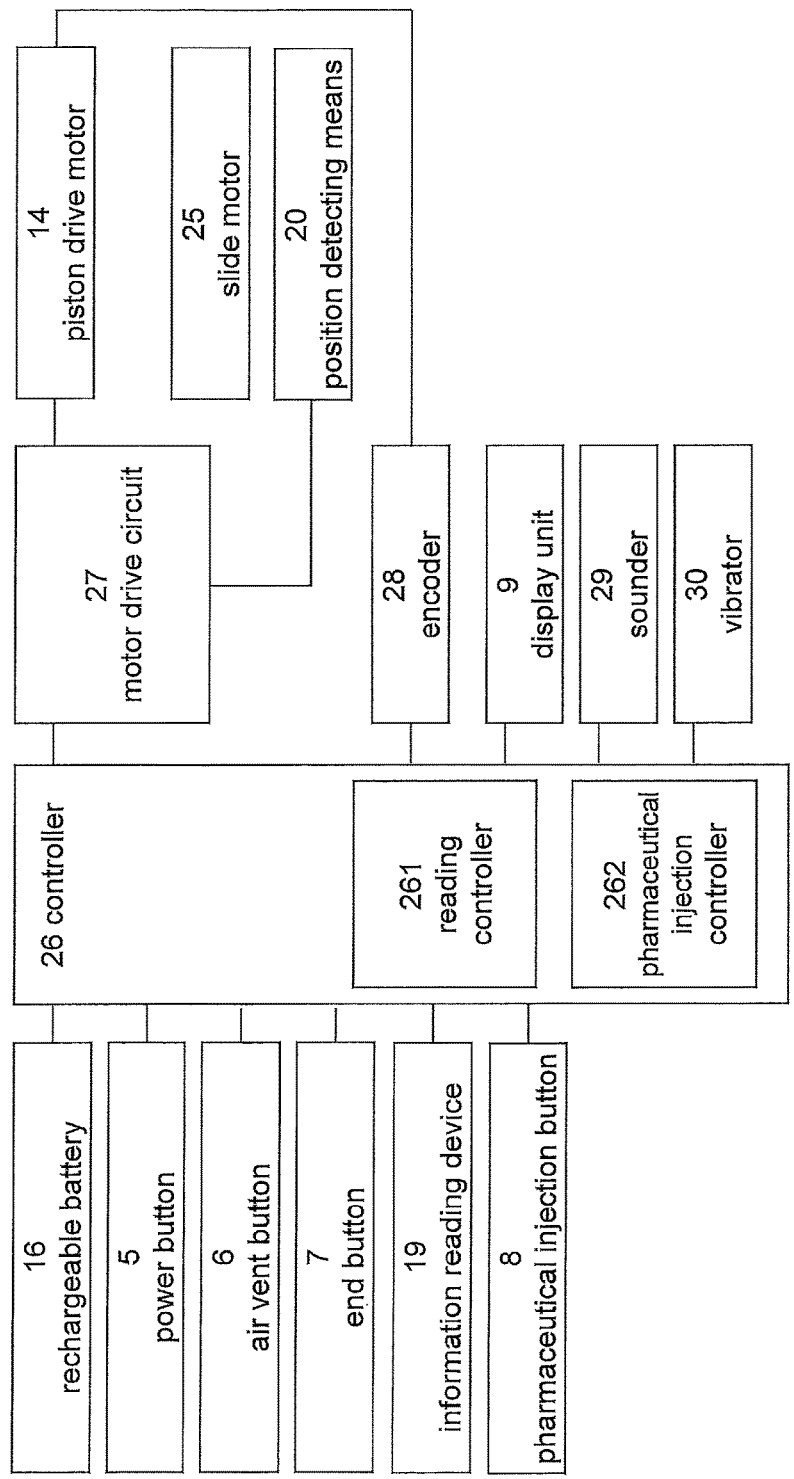
FIG. 4 is a control block diagram of the pharmaceutical injection device in Embodiment 1 pertaining to the present invention.

FIG. 4 shows the electrical control blocks, and as shown in FIG. 4, the power button 5, the air vent button 6, the end button 7, the pharmaceutical injection button 8, the display unit 9, and the information reading device 19 are connected to a controller 26. The piston drive motor 14, the slide motor 25, and the position detecting means 20 are connected to the controller 26 via a motor drive circuit 27. The amount of drive of the piston drive motor 14 is transmitted through an encoder 28 to the controller 26. The amount of charge of a rechargeable battery 16 is also transmitted to the controller 26. Furthermore, a sounder 29 and a vibrator 30 are connected as warning means to the controller 26.

A reading controller 261 that controls the information reading device 19, and a pharmaceutical injection controller 262 that controls pharmaceutical injection on the basis of the information thus read are provided to the controller 26. If it is determined from the information that has been read that the pharmaceutical was not injected properly, the pharmaceutical injection controller 262 issues a warning from the sounder 29 and the vibrator 30, and controls the pharmaceutical injection button 8 to stop the injection of pharmaceutical.

Operation of Pharmaceutical Injection Device

Next, the operation of the pharmaceutical injection device in this embodiment will be described through reference to FIGS. 1 to 4.

When pharmaceutical is to be injected, first the user presses the air vent button 6 to drive the slide motor 25. This pushes the case 24 forward and moves the inner case 11 forward along with the pharmaceutical syringe 10. Consequently, the injection needle 12 sticks out from the distal end opening 13 of the distal end cap 3. In the next instant, the piston unit 15 is pushed forward by the piston drive motor 14. This causes part of the pharmaceutical in the pharmaceutical syringe 10 to be sprayed out of the distal end of the injection needle 12, and air venting is thus complete.

Once this air venting is finished, the slide motor 25 is reversed, and the inner case 11 also retracts. Consequently, the injection needle 12 goes back inside the distal end cap 3. Since air venting is complete at this point, the end button 7 is pressed, and then the pharmaceutical injection button 8 is pressed for pharmaceutical injection. This drives the slide motor 25 and pushes the case 24 forward, so that the inner case 11 moves forward along with the pharmaceutical syringe 10. Consequently, the injection needle 12 sticks out of the distal end opening 13 and punctures the skin of the patient.

In the next instant, the piston unit 15 is pushed forward by the piston drive motor 14. This causes a specific amount of the pharmaceutical in the pharmaceutical syringe 10 to be sprayed out of the injection needle 12, and the injection of pharmaceutical is thus complete.

When the injection of pharmaceutical is complete, the slide motor 25 reverses and the inner case 11 also retracts. This causes the injection needle 12 to go back inside the distal end cap 3.

The injection of pharmaceutical is complete after the above operation, so the power button 5 is pressed to switch off by the power.

For the next pharmaceutical injection, the user presses the power button 5 to switch on the power, and the above operation is repeated.

The information recording medium 17 for checking the type and quantity of pharmaceutical to be injected, etc., prior to the actual pharmaceutical injection operation, the pharmaceutical syringe 10 to which this information recording medium 17 is affixed, the information reading device 19 for reading this information recording medium 17, and so forth will now be described.

Pharmaceutical Syringe

As shown in FIG. 5A, the pharmaceutical syringe 10 (an example of a columnar body) comprises a pharmaceutical syringe main body 100 (an example of a columnar main body) and the information recording medium 17 that is wound and fixed around the outer peripheral face at the rear part of the pharmaceutical syringe main body 100. The "rear part" here refers to the side on which the piston unit 15 is provided, and the front part is the side on which the injection needle 12 of the pharmaceutical syringe 10 is provided when mounted to the pharmaceutical injection device 1.

Information Reading Device

In this embodiment, an information symbol (see 18 in FIGS. 6A and 6B) on the information recording medium 17 of the pharmaceutical syringe 10 is read by the information reading device 19 shown in FIG. 3.

More specifically, as shown in FIG. 5B, the information reading device 19 comprises a light emitting element 31 that emits light at a strip-form information recording medium 17 affixed to the outer peripheral face of the pharmaceutical syringe main body 100 (an example of a columnar main body), a light receiving element 32 that receives reflected light from the information recording medium 17, and the controller 26 (including the reading controller 261) connected to the light receiving element 32.

Information Recording Medium

As shown in FIG. 6A, the information recording medium 17 comprises a slender sheet-form member 33 and a plurality of the same information symbols 18 displayed on the surface 33a of the sheet-form member 33. One end and/or the other of the sheet-form member 33 in the longitudinal direction is provided with an edge line 34 formed in a direction perpendicular to the longitudinal direction.

The information recording medium 17 is configured such that a center line 35 that is substantially perpendicular to the edge line 34 is provided to the center axis portion of the sheet-form member 33 in the longitudinal direction, and a plurality of the information symbols 18 are disposed on both sides of this center line 35.

Furthermore, start marks 36 are provided on both sides of the center line 35. As shown in FIG. 6A, the information symbols 18 are displayed from the start marks 36 on both sides of the center line 35. In this embodiment, the information symbols 18 are displayed to the right from the start marks 36. As an example, the start mark 36 of the information symbol 18X shown in FIG. 6A are indicated by 36X.

As shown in FIG. 6B, when the slender sheet-form member 33 constituting the information recording medium 17 is affixed to the columnar pharmaceutical syringe main body 100, the two ends of the sheet-form member 33 overlap, creating a state in which part of the edge line 34 overlaps an information symbol 18.

The square enclosed by dotted lines in FIGS. 6A and 6B indicates a reading area 37 of the information reading device 19. The information symbols 18 present within this square are read by the information reading device 19.

The affixing of the information recording medium 17 to the pharmaceutical syringe main body 100 will now be described. As shown in FIG. 6A, the end on the right side of the information recording medium 17 is indicated as 33R, and the end on the left side as 33L.

As shown in FIG. 7A, the right end 33R side of the sheet-form member 33 is affixed to the surface of the pharmaceutical syringe main body 100, after which the sheet-form member 33 is wound around and affixed to the pharmaceutical syringe main body 100 so that the left end 33L side overlaps the surface 33a. As shown in FIG. 7C, which is a detail view of the S part in FIG. 7A, an adhesive layer 33b is provided to the rear side of the sheet-form member 33, allowing this member to be affixed to the surface of the pharmaceutical syringe main body 100.

FIG. 7D shows a cross section of the pharmaceutical syringe 10 in the reading area 37 of the information reading device 19. As shown in FIG. 7D, since the pharmaceutical syringe 10 is a columnar body (in the form of a circular column) as mentioned above, the inside of the reading area 37 is in the form of a spherical surface. Therefore, even though there are a plurality of information symbols 18 within the reading area 37, in terms of stable reading it is important for the information symbols 18 to be read as close to the center portion as possible. Specifically, if the information reading device 19 is disposed in the center of the reading area 37, and an information symbol 18 that is close to the light receiving element 32 of the information reading device 19 is selected out of the plurality of information symbols 18, then the information symbol that is as flat as possible will be selected, which improves reading stability.

However, as shown in FIGS. 6B and 7B, if the edge line 34 happens to be within the reading area 37, this edge line 34 can be avoided and an information symbol 18 that is nearby can be read.

That is, even if an information symbol 18 is present in the center portion of the reading area 37, it will be incomplete as an information symbol 18 if it is covered by the edge line 34, so the information symbol 18 that is covered by the edge line 34 is avoided, and an information symbol 18 that is nearby and not covered by the edge line 34 is read. The phrase "covered by the edge line 34" encompasses a state in which at least part of the information symbol 18 is covered by the edge line 34, as well as a state in which at least part of the information symbol 18 is printed, coated, etc., with the edge line 34.

The expiration date, the pharmaceutical name, and so forth are recorded with this information symbol 18. Therefore, if the expiration date and pharmaceutical name are correct, the controller 26 allows the injection of pharmaceutical described above, but if the expiration date or pharmaceutical name is incorrect, a warning is issued from the sounder 29 and vibrator 30 used as warning means, and the pharmaceutical injection operation ends up being halted. More precisely, the expiration date, the pharmaceutical name, etc., on the information symbol 18 are read by the reading controller 261 as described above, and the pharmaceutical injection controller 262 issues a warning from the sounder 29 and the vibrator 30 and halts the pharmaceutical injection operation.

Information Reading Method

The operation of this information reading device will be described in further detail through reference to the flowchart in FIG. 8.

Figure 8:
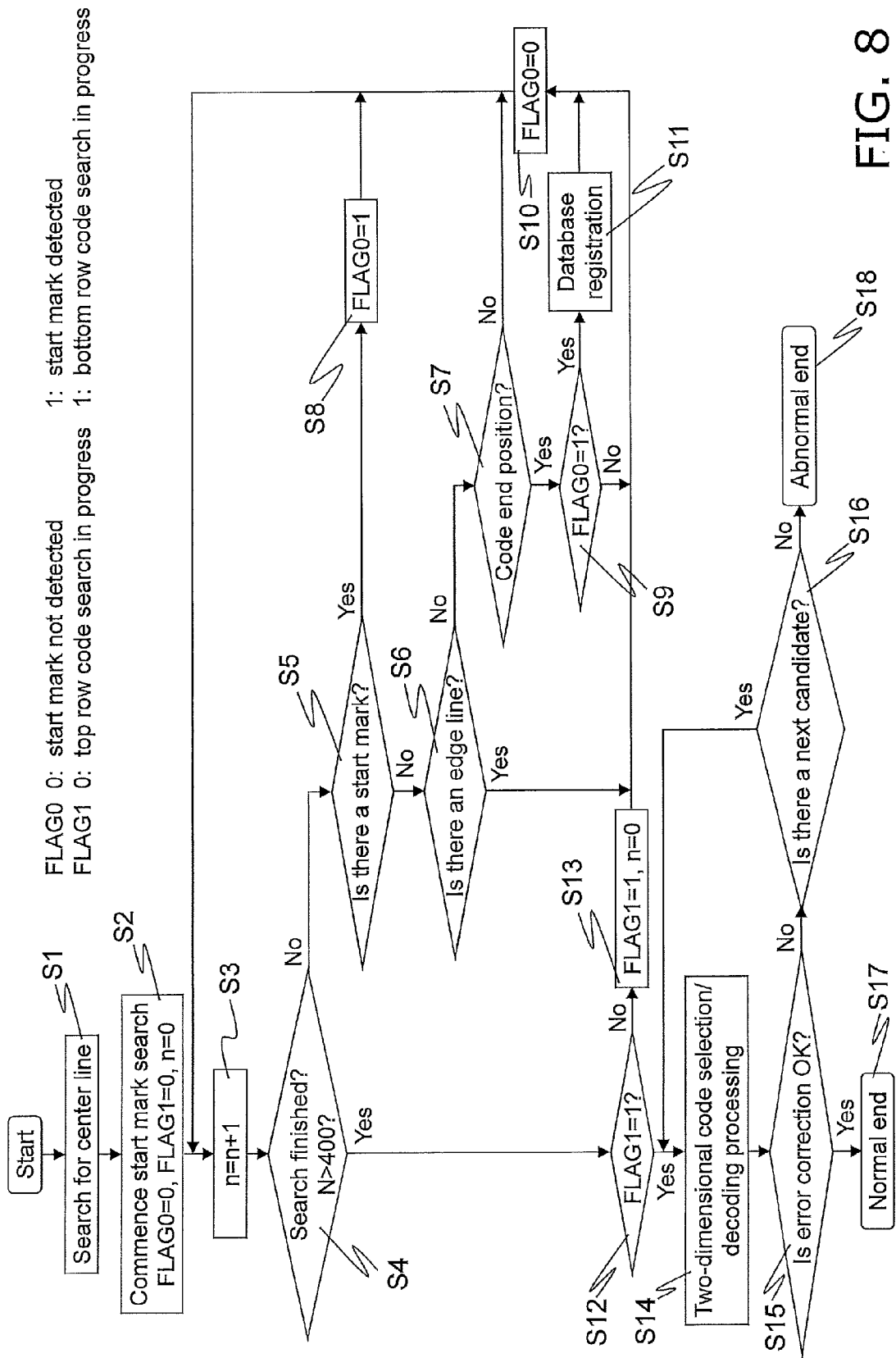
FIG. 8 is an operation flowchart of the information reading device in Embodiment 1 pertaining to the present invention.

The reading controller 261 in the controller 26 searches for whether or not there is a center line 35 among the data read by the light receiving element 32 from the reading area 37 (S1 in FIG. 8). Next, setting that a start mark 36 has not been detected, and setting that reading is to be started from the top row are performed (S2 in FIG. 8). The job of detecting the start marks 36 involves dividing both the top and bottom rows of the reading area 37 into 400 areas from the left end to the right end in FIGS. 6A and B, and then detecting one area at a time going from the left side to the right side. The result of this is that detection of the start marks 36 is carried out 400 times in both the top row and the bottom row. In this Specification, the n-th divided area from the left out of the 400 divided areas obtained by dividing the reading area 37 into 400 areas is denoted as n/400.

When the above-mentioned settings are made in S2, the control processing moves on to S3. The divided areas are gone through in S3. That is, moving on to the next divided area moves the divided area read by the information reading device one area to the right. Since n=0 at first, one move in S3 results in n=1, and the divided area located to the far left in the reading area 37 is detected.

In S4, detection is carried out 400 times each in the top and bottom rows. First, in S2 the setting is made that reading is to be started from the top row (FLAG1=0 in S2), so on the top row side the control processing then moves on to S5.

In S5 it is determined each time whether or not there is a start mark 36 in that detection portion. In the state in FIG. 6B, there is no start mark 36 in the portion at the left end, so the control processing moves on to S6.

In S6, it is determined whether or not the edge line 34 is in this 1/400 divided area. In the state shown in FIG. 6B, the edge line 34 is not present in the portion at the left end, so the control processing moves on to S7.

In S7, the code end position is confirmed (the code end position refers to the position where the information symbol 18 ends from the start mark 36, that is, the width of the information symbol 18). This confirmation of the code end position is accomplished by detecting the end position of the information symbol 18 from the difference in reflectivity, and does not take into account the distance from the start mark 36 (the width of the information symbol 18). The reason for this is that even if the computation factors in the distance, for example, since the sheet-form member 33 is affixed to the pharmaceutical syringe main body 100 that is in the form of a circular columnar body, when an image is captured with an imaging element, the farther the image is to the left or right from the center 37$a$ of the reading area 37, the most compressed it will be, making it difficult to measure the distance correctly.

In the state of the left end of the reading area 37 shown in FIG. 6B, there is no code end position of the information symbol 18, so the control processing moves back to S3 at this point.

Then, in S3, the divided area that is read is moved from the $1^{st}$ (1/400) to the $2^{nd}$ (2/400). In S4, it is determined whether or not all 400 of the divided areas have been read, so the control processing moves on to S5.

Then, in S6, it is determined whether or not the edge line 34 is in the 2/400 divided area by performing this second detection. In the state in FIG. 6B, the edge line 34 is not in this 2/400 divided area either, so the control processing moves on to S7. In S7 the code end position is checked, but since the code end position of the information symbol 18 is not present in the state at this area, the control processing moves back to S3.

Detection is carried out 400 times in this manner.

In the course of performing detection 400 times (while the divided area moves successively to the right in a control loop comprising S3, S4, S5, S6, S7, and then returning to S3), if the start mark 36$a$ in FIG. 6B is detected in S5, the control processing moves from S5 to S8. In S8 the start mark 36$a$ is deemed to have been detected (FLAG0=1), and the control processing moves back to S3.

The loop of S3, S4, S5, S6, S7, and then returning to S3 is then repeated, and if the code end position is confirmed in S7 while the detected divided area successively moves to the right, the control processing moves on to S9. In S9 it is determined whether or not the start mark 36$a$ has been confirmed (FLAG0=1). If it has been determined that the start mark 36$a$ has been confirmed, the control processing moves on to S11, and the information symbol 18 is deemed valid and is registered in the database in the reading controller 261. However, in the state shown in FIG. 6B, during reading of the divided area while successively moving to the right after the start mark 36$a$ is detected, the presence of the edge line 34 is confirmed in S6. Therefore, the FLAG0 is set to 0 in S10, it is concluded that no start mark 36$a$ was detected (FLAG0=0), and the control processing moves back to S3.

After this, when reading in the divided area is carried out while moving to the right, a start mark 36$b$ is again detected in the top row. When this happens, during reading of the divided area while moving to the right, the control processing moves from S5 to S6, S7, and S9, and in S11 the information symbol 18 in the top row is registered.

When detection has thus been carried out 400 times in the top row, the control processing moves from S4 to S12. In S12 it is determined whether or not detection is in progress in the bottom row. At the point when detection has been performed 400 times in the top row, detection has not been carried out in the bottom row, so in S12 it is determined that detection is not in progress in the bottom row. Accordingly, the control processing moves on to S13, and since detection is in progress in the bottom row, the flag 1 is changed to 1 (FLAG1=1). Then, in S10, the FLAG0 is changed to 0 (FLAG0=0), and the control processing moves as needed from S4 to S11 to carry out detection in the bottom row.

In the state in FIG. 6B, of the information symbols 18 in the bottom row of the reading area 37, the ones located at the left and right ends are only partly present in the reading area 37. Also, those on the inside are covered by the edge line 34. More precisely, the left portion of the information symbol 18$o$ present at the left end of the bottom row is not in the reading area 37, so the start mark 36 cannot be read. The right portion of the information symbol 18$p$ present at the right end of the bottom row is missing, so although the start mark 36 can be read, the code end position is unconfirmed. The information symbol 18$q$ disposed on the right side of the edge line 34 is printed with the edge line 34 superposed over it, and since it is printed on the sheet-form member 33 with part of it cut off by the end, the start mark 36 cannot be read. Also, the information symbol 18$r$ disposed on the left side of the edge line 34 is partly covered by the portion on the left end 33L side of the sheet-form member 33 where the edge line 34 is located, so the edge line 34 is read after the start mark 36 is read. As mentioned above, the information symbols 18$o$, 18$p$, 18$q$, and 18$r$ in the bottom row are not registered to the database.

Accordingly, there is no information symbol 18 in the bottom row that can be registered in S11.

Consequently, the information symbol 18 disposed further to the right than the edge line 34 in the top row is registered to the database (see c in the drawing). S2 to S13 in which this registered information symbol 18 is selected corresponding to an example of the first information symbol selection step.

On the other hand, when an information symbol 18 in the bottom row can also be registered, after detection has been performed 400 times in the bottom row, in S14 an information symbol 18 is selected, using as the basis for determination which of the information symbol 18 in the top row and the information symbol 18 in the bottom row is closer to the center of the reading area 37. This selection in S14 corresponds to an example of the second information symbol selection step.

That is, as shown in FIG. 7D, since the information symbols 18 in the reading area 37 have a curved surface, the closer they are to the center of the reading area 37 (see the center 37$a$ shown in FIGS. 6A and 6B), the more they can be read in planar fashion by the information reading device 19. Data about the top row or bottom row information symbol 18 thus selected is checked for error correction in S15. If error correction is not appropriate, in S16 the control processing returns to S14 to select the next candidate. That is, if the information symbol 18 selected in S14 has been soiled, for example, then the proper data cannot be read from it. Accordingly, in S14, the information symbol 18 next closest to the reading area 37 after the previously selected information symbol 18 is selected, and its data is read (S16). The decoding processing in S14 corresponds to an example of the information acquisition step.

More specifically, the X coordinate of the start mark 36 of each information symbol 18 is registered to the database. This database includes the X coordinates of the start marks 36 of the various information symbols 18, and the distance from the center 37$a$ of the reading area 37 of each information symbol 18 is computed from the X coordinates of these start marks 36. More specifically, since the reading area 37 is divided into 400 areas, there are 200 X coordinates of the center 37$a$. With information symbols 18 located to the right of the center 37$a$, the positions of the start marks 36 thereof indicate the distance from the center. More specifically, if there are, for example, 240 X coordinates of the start mark 36 of the information symbol 18 indicated by c in FIG. 6A, the distance from the center 37a of that information symbol 18 is found by 240−200, or 40.

Meanwhile, in code regions located to the left of the center, the right side of the code region, rather than the start mark 36 side, is the distance from the center. For example, if we assume that the width of the information symbols 18 is set to 152, and that there is an information symbol 18 for which the X coordinate of the start mark 36 is 3, then the distance from the center 37a of that information symbol 18 is found by 200−(3+152), or 45. Therefore, the information symbol 18 for which the distance from the center 37a is 40 is selected as the information symbol 18 closest to the center 37a.

In S16, if there is no next candidate, in S18 it is deemed that there is an abnormality, and the operation is ended. At this point a message to the effect that the content of the pharmaceutical syringe 10 cannot be confirmed is displayed on the display unit 9. Naturally, pharmaceutical cannot be injected in this case.

Furthermore, even if the data can be read, if the type of pharmaceutical is different, or if the expiration date has been exceeded, here again this status is displayed on the display unit 9, and control is performed so that pharmaceutical cannot be injected. Specifically, if the pharmaceutical injection controller 262 gives an instruction that prohibits pharmaceutical injection, then control is performed so that the slide motor 25 will not operate even if the pharmaceutical injection button 8 is pressed, for example.

Action and Effects

As discussed above, there are provided a slender sheet-form member and a plurality of the same information symbols that are displayed on the surface of this sheet-form member, and an edge line is provided on one end side and/or the other end side of the sheet-form member, so the information symbol can be properly read.

Specifically, since the edge line is provided to one end side and/or the other end side of the sheet-form member, an information symbol that is not covered by the edge line can be read, and as a result the information symbol can be read properly.

Using FIG. 6B to describe a case in which there is no edge line 34, since the code end position of the information symbol 18q is detected after the start mark 36 of the information symbol 18r is detected, an information symbol that integrates the information symbols 18r and 18q with missing information may end up being determined to be valid as a single information symbol, and be subjected to decoding.

However, if the edge line 34 is provided and detected as in this embodiment, the information symbols 18r and 18q will not be registered to the database, and will therefore not be subjected to decoding, so the information can be read properly.

Also, when a plurality of information symbols are selected, the one located closest to the light receiving element 32 of the information reading device 19 can be selected and read, allowing more accurate information to be read.

Also, if selection processing is performed again when an error is found, the user does not need to remount the pharmaceutical syringe 10, rotate the pharmaceutical syringe, or the like, which means that less burden is imposed on the user.

Embodiment 2

Embodiment 2 of the present invention will be described through reference to FIGS. 9 to 16.

In Embodiment 2, an information symbol 18 is divided into four code regions (an example of an area of an information symbol). To make it easier to understand the following description, the information symbols 18 present in the reading area 37 are displayed as A (code regions A1, A2, A3, and A4), B (code regions B1, B2, B3, and B4), C (code regions C1, C2, C3, and C4), D (code regions D1, D2, D3, and D4), E (code regions E1, E2, E3, and E4), F (code regions F1, F2, F3, and F4), and G (code regions G1, G2, G3, and G4). Specifically, code regions A1, B1, C1, D1, E1, F1, and G1 are regions indicating the same information, A2, B2, C2, D2, E2, F2, and G2 are code regions indicating the same information, A3, B3, C3, D3, E3, F3, and G3 are code regions indicating the same information, and code regions A4, B4, C4, D4, E4, F4, and G4 are code regions indicating the same information.

With this information recording medium 17, when the slender sheet-form member 33 is affixed to the columnar pharmaceutical syringe main body 100, as shown in FIG. 9B, one end of this sheet-form member 33 overlaps the other end, resulting in a state in which the edge line 34 overlaps part of the information symbols 18.

Also, since each information symbol 18 is divided in four, the code regions A2, A3, A4, B1, C1, C2, C3, and C4 are in the top row, and the code regions D4, E1, E2, E3, F3, F4, G1, and G2 are in the bottom row. When the information symbols 18 are thus divided in four, the start marks 36 are the same for A1, B1, C1, D1, E1, F1, and G1, the same for A2, B2, C2, D2, E2, F2, and G2, the same for A3, B3, C3, D3, E3, F3, and G3, and the same for A4, B4, C4, D4, E4, F4, and G4. Naturally, within the A group, the B group, the C group, the D group, the E group, the F group, and the G group, the start marks 36 are different, as shown in FIG. 9 (the widths in the longitudinal direction of the sheet-form member 33 are different).

Figure 9:
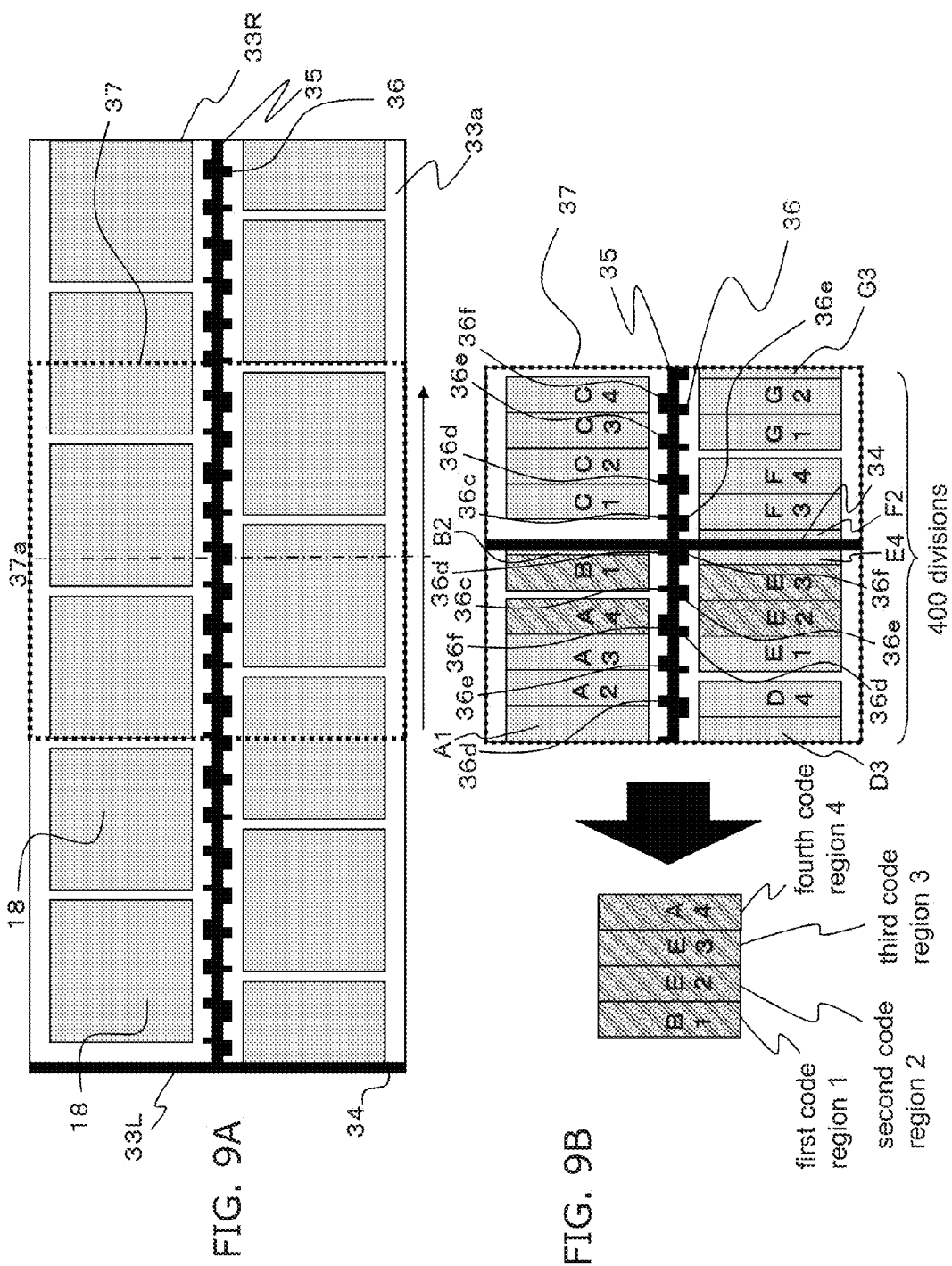
FIG. 9A is a plan view of the information recording medium in Embodiment 2 pertaining to the present invention.
FIG. 9B is a front view of the state when the information recording medium has been affixed to the pharmaceutical syringe in Embodiment 1 pertaining to the present invention.

In FIG. 9, information is read from the information symbol 18 closest to the center of the reading area 37 (see the center 37a in FIG. 9A (in FIG. 9B, the center 37a is not shown because it makes the drawing harder to view). In Embodiment 2, however, since the information symbols 18 are divided in four, B1 is selected as the first code region (A1, B1, C1, D1, E1, F1, and G1), E2 is selected as the second code region (A2, B2, C2, D2, E2, F2, and G2), E3 is selected as the third the code region (A3, B3, C3, D3, E3, F3, and G3), and A4 is selected as the fourth code region (A4, B4, C4, D4, E4, F4, and G4). The information symbols 18 can be read by integrating these. The selected code region corresponds to an example of the region of the information symbols selected as the information region.

Information Reading Operation

Next, this reading operation will be described in detail through reference to the drawings.

Figure 10:
FIG. 10 is an operation flowchart of the information reading device in Embodiment 2 pertaining to the present invention.
Figure 11:
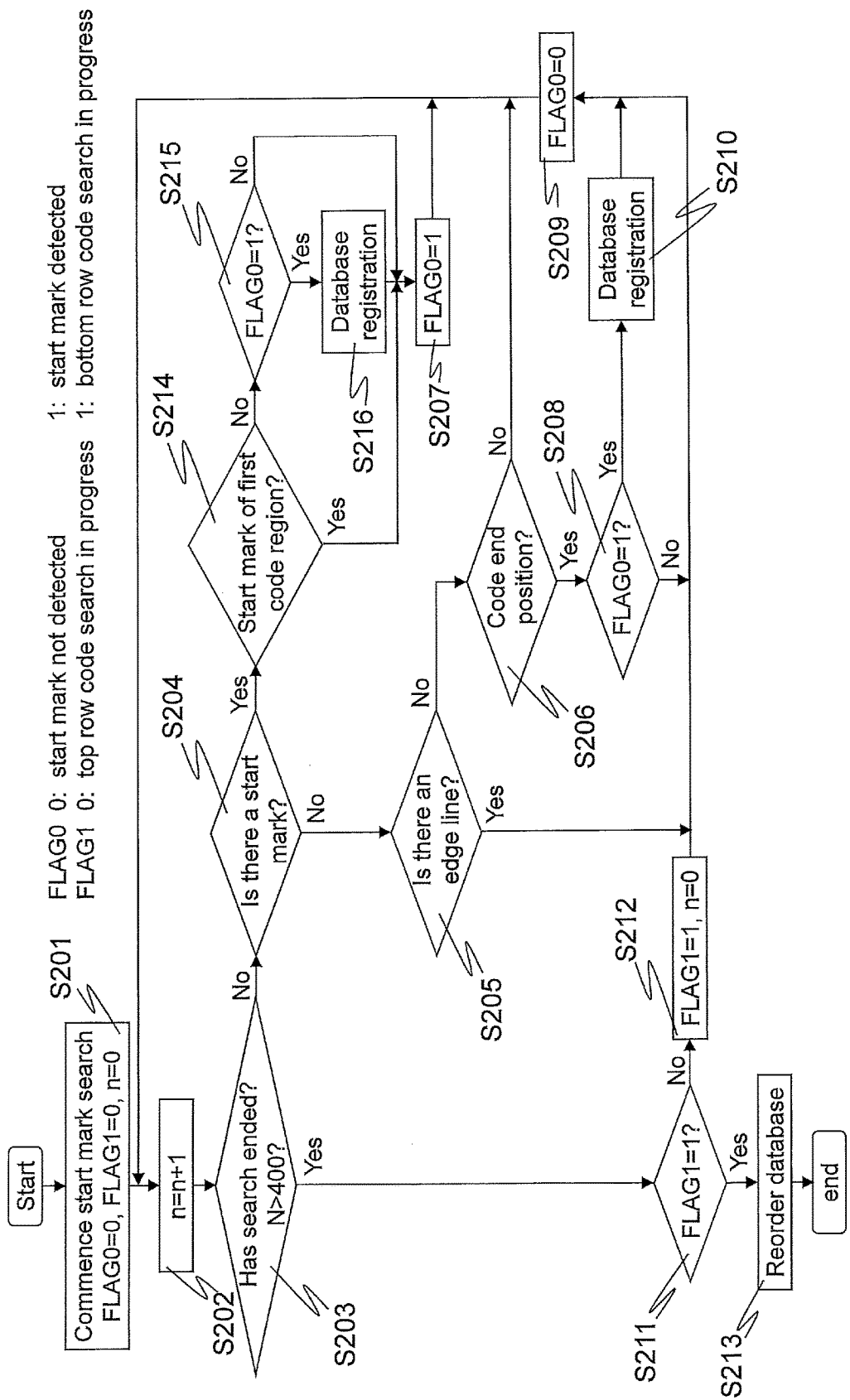
FIG. 11 is an operation flowchart of the information reading device in Embodiment 2 pertaining to the present invention.

First, the reading controller 261 (see FIG. 4) searches the data read by the light receiving element 32 from the area 37 to see if the center line 35 in FIG. 9 is present (S101 in FIG. 10). Next, database production processing is performed (S102 in FIG. 10). More specifically, this database production processing involves executing the flow shown in FIG. 11. As shown in FIG. 11, the database production processing entails performing setting that a start mark 36 has not been detected, and setting that reading is to be started from the top row (S201 in FIG. 11).

The job of detecting the start marks 36 involves dividing both the top and bottom rows of the reading area 37 into 400 areas from the left end to the right end in FIGS. 9A and 9B, and then detecting one area at a time going from the left side to the right side. The result of this is that detection of the start marks 36 is carried out 400 times in both the top row and the bottom row.

When the above-mentioned settings are made in S201, the control processing moves on to S202. The divided areas are gone through in S202. That is, moving on to the next divided area moves the divided area read by the information reading device 19 one area to the right.

In S203, detection is carried out 400 times each in the top and bottom rows. First, in S201 the setting is made that reading is to be started from the top row (FLAG1=0 in S201), so on the top row side the control processing then moves on to S04.

In S204, it is determined whether or not a start mark 36 from the A group, the B group, the C group, the D group, the E group, the F group, or the G group is present in the detection portion each time. In the state in FIG. 9B, there is no start mark 36 for any of the A group, the B group, the C group, the D group, the E group, the F group, or the G group in the portion at the left end, so the control processing then moves on to S205.

In S205 it is determined whether or not the edge line 34 is in this ¹⁄₄₀₀ divided area. In the state in FIG. 9B, the edge line 34 is not present in the portion at the left end, so the control processing moves on to S206.

In S206, the code end position is confirmed (the code end position refers to the position where the information symbol 18 ends, that is, the width of the information symbol 18). This confirmation of the code end position is accomplished by detecting the end position of the information symbol 18 from the difference in reflectivity, and does not take into account the distance from the start mark 36 (the width of the information symbol 18).

In the state of the left end of the reading area 37 shown in FIG. 9B, there is no code end position corresponding to any of the A group, the B group, the C group, the D group, the E group, the F group, or the G group divided in four, so at this point the control processing moves back to S202.

Then, in S202, the divided area that is read is moved from the 1$^{st}$ (¹⁄₄₀₀) to the 2$^{nd}$ (²⁄₄₀₀). In S203, it is determined whether or not all 400 of the divided areas have been read, but since not all of the divided areas have been read yet, the control processing moves on to S204.

Then, in S205, it is determined whether or not the edge line 34 is in the ²⁄₄₀₀ divided area by performing this second detection. In the state in FIG. 9B, the edge line 34 is not in this ²⁄₄₀₀ divided area either, so the control processing moves on to S206. In S206 the code end position is checked, but since the code end position is not present in the state at this left end, the control processing moves back to S202.

Detection is carried out 400 times in this manner.

In the course of performing detection 400 times (while the detected divided area moves successively to the right in a control loop comprising S202, S203, S204, S205, S206, and then returning to S202), if the start mark 36 is detected in S204, the control processing proceeds to S214. In S214 it is determined whether or not the detected start mark 36 is the start mark 36c in the first code region. If it is the start mark 36c in the first code region, the control processing moves on to S207, and the start mark 36 is set as detected (FLAG0=1). The control processing then moves on to S202. Meanwhile, if it is determined in S214 that the detected start mark 36 is not the start mark 36c of the first code region, the control processing moves on to S215, and it is determined whether or not a start mark detected flag (FLAG0=1) has been set. If the start mark detected flag (FLAG0=1) has not been set, the control processing moves on to S207, and a start mark detected flag (FLAG0=1) is set. On the other hand, if in S215 it is determined that a start mark detected flag (FLAG0=1) has been set, the code region located to the left of the start mark detected this time is registered as valid in the database of the reading controller 261.

In the state shown in FIG. 9B, the start mark 36d of the second code region A2 of the information symbol 18A divided in four and shown in FIG. 9B is detected. The control processing then moves from S204 to S214. Since the detected start mark is not the start mark 36c of the first code region, the control processing moves on to S207, and the start mark 36 is set to detected (FLAG0=1). After the start mark 36d of the second code region A2 is detected, a loop comprising S202, S203, S204, S205, S206, and back to S202 again is repeated, during which the start mark 36e of the third code region A3 is detected in S204. Since the detected start mark 36e is the start mark of the third code region, the control processing moves from S214 to S215. Here, when the start mark 36d of the second code region A2 is detected, since the start mark is set to detected (FLAG0=1), the control processing moves on to S216, and the second code region A2 is registered as valid in the database of the reading controller 261. The loop of S202, S203, S204, S205, S206, and then returning to S202 is repeated, and while this loop is being repeated, the start mark 36f is confirmed in S204, and the third code region A3 is registered as valid in the database of reading controller 261 in the same steps as above.

Next, the loop of S202, S203, S204, S205, S206, and then returning to S202 is repeated. While this loop is being repeated, if the code end position (the end position of the information symbol 18) is confirmed in S206, the control processing moves on to S208. In the state shown in FIG. 9B, the end position of the information symbol A (can also be called the end position of the code region A4) is confirmed.

In S208, it is determined whether or not the start mark 36 has been confirmed (FLAG0=1). If it is determined that the start mark 36 has been detected, the control processing moves on to S210, and this is registered to the database of the reading controller 261 as a valid code region. In the state shown in FIG. 9B, since a start mark detected (FLAG0=1) has been set in S207 during detection of the start mark 36f, the code region A4 is registered to the database as a valid code region.

After this, the control processing moves on to S209, and a setting of an undetected state of the start mark 36 (FLAG0=0) is made.

Thus, in Embodiment 2, the start mark for the code region that is read next (the second to fourth code regions) is used to detect the end of the code region for the first to third code regions. For the fourth code region, the end of the code region is detected by using the end position of the information symbol 18 (A, B, C, D, E, F, or G), just as in Embodiment 1.

Next, in the state shown in FIG. 9B, while the loop of S202, S203, S204, S205, S206, and then returning to S202 is being repeated, the start mark 36c of the code region B1 is detected in S204, and the control processing moves on to S214. Since the detected start mark is the start mark 36c of the first code region, the control processing moves on to S207, and the flag is set to start mark detected (FLAG0=1). Then, when the start mark 36d of the code region B2 is detected in S204 during the repetition of the above-mentioned loop, the control processing moves on to S214, S215, and S216, and the code region B1 is registered to the database as valid.

By repeating detection 400 times in the top row as above, more specifically the code regions A2, A3, A4, B1, C1, C2, C3, and C4 are registered as information symbols 18 divided in four in the top row. In the state in FIG. 9B, after the detection of the code regions A2, A3, A4, and B1, the start mark 36d of the code region B2 is detected, but the presence of the edge line 34 is confirmed in S205 in the detection of the following divided area. Accordingly, in S209 the start mark 36d is deemed not to have been detected (FLAG0=0), and the control processing moves to S202.

Once detection has thus been completed 400 times in the top row, the control processing moves from S203 to S211. In S211 it is determined whether or not detection is in progress in the bottom row. At the point when detection has been performed 400 times in the top row, detection has not been carried out in the bottom row, so in S211 it is determined that detection is not in progress in the bottom row. Accordingly, the control processing moves on to S212, and since detection is in progress in the bottom row, the FLAG1 is changed to 1 (FLAG1=1). Then, in S209, the FLAG0 is changed to 0 (FLAG0=0), and the control processing moves as needed from S202 to S210 and from S202 to S216 to carry out detection in the bottom row.

In the state in FIG. 9B, of the information symbols 18 in the bottom row of the reading area 37, the code regions D3 and G3 located at the left and right ends are only partly present, and E4 and F2 on the inside are covered by the edge line 34, so of the information symbols 18 divided in four, D3, G3, F2, and E4 cannot be registered in S210 from the bottom row. More precisely, the left portion of the code region D3 is not in the reading area 37, so the start mark 36e cannot be read. The right portion of the code region G3 is missing, so although the start mark 36e can be read, the next start mark 36f cannot be read. The code region F2 disposed on the right side of the edge line 34 is printed with the edge line 34 superposed over it, and since it is printed on the sheet-form member 33 with part of it cut off by the end, the start mark 36d cannot be read. Also, code region E4 disposed on the left side of the edge line 34 is partly covered by the portion on the left end 33L side of the sheet-form member 33 where the edge line 34 is located, so the edge line 34 is read. Therefore, the code regions D3, G3, F2, and E4 are not registered to the database.

However, the code regions D4, E1, E2, E3, F3, F4, G1, and G2 in the bottom row can be registered as information symbols 18. As discussed above, S205 to S210 and S214 to S216 for selecting the code regions to be registered correspond to an example of the first information symbol selection step.

Next, in S213 in FIG. 11, the code region closest to the center 37a of the reading area 37 is selected for every four code regions from among the registered top row code regions A2, A3, A4, B1, C1, C2, C3 and C4, and bottom row code regions D4, E1, E2, E3, F3, F4, G1 and G2.

More specifically, in the situation shown in FIG. 9, since the code regions B1, C1, E1, and G1 are registered as the first code regions (A1, B1, C1, C1, E1, F1, and G1), the code region B1 is selected from among these as the one closest to the center 37a of the reading area 37.

Next, since the code regions A2, C2, E2, and G2 are registered as the second code regions (A2, B2, C2, D2, E2, F2, and G2), the code region E2 is selected from among these as the one closest to the center 37a of the reading area 37.

Further, since the code regions A3, C3, E3, and F3 are registered as the third code regions (A3, B3, C3, D3, E3, F3, and G3), the code region E3 is selected from among these as the one closest to the center 37a of the reading area 37.

In addition, since the code regions A4, C4, D4, and F4 are registered as the fourth code regions (A4, B4, C4, D4, E4, F4, and G4), the code region A4 is selected from among these as the one closest to the center 37a of the reading area 37.

That is, since the registered first code regions B1, C1, E1, and G1 are put into a database form as indicated by the database 38 in FIG. 13A, the code region B1 is selected from among these as the one closest to the X coordinate (200) of the center 37a of the reading area 37.

The database 38 in FIG. 13A shows the X coordinates for the start marks of the various code regions, and the distance of each code region from the center 37a of the reading area 37 is computed from these start mark X coordinates. More specifically, since the reading area 37 is divided into 400 areas, the X coordinate of the center is 200. In code regions located on the right side of the center 37a, the position of the start marks thereof indicates the distance from the center 37a. More specifically, in FIG. 13A, the code region C1 is located to the right of the center 37a, and its distance from the center 37a is found by 238−200, or 38. The code region G1 is also located to the right of the center 37a, and its distance from the center 37a is found by 314−200, or 114.

Meanwhile, in code regions located to the left of the center 37a, the right side of the code region, rather than the start mark side, is the distance from the center. In this embodiment, the width of each code region in which the information symbol 18 is divided in four is set to 38. More specifically, in FIG. 13A, the code region B1 is located to the left of the center 37a, and its distance from the center 37a is found by 200−(162+38), or 0. The code region E1 is also located to the left of the center 37a, and its distance from the center 37a is found by 200−(76+38), or 86.

Figure 15:
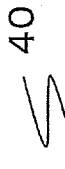
FIG. 15 shows a database of the information reading device in Embodiment 2 pertaining to the present invention.
Figure 16:
FIG. 16 shows a database of the information reading device in Embodiment 2 pertaining to the present invention.

Specifically, as shown in FIG. 13B, in the example shown in FIG. 13A it can be seen that the distance of the code regions B1, C1, E1, and G1 from the center increases in that order. In FIGS. 14, 15, and 16 mentioned later, the distance of the code regions from the center 37a is similarly computed, and the distances of the code regions from the center 37a are determined in order.

Since the registered second code regions A2, C2, E2, and G2 are put into a database form as indicated by the database 39 in FIG. 14, the code region E2 is selected from among these as the one closest to the X coordinate (200) of the center 37a of the reading area 37.

Further, since the code regions A3, C3, E3, and F3 are put into a database form as indicated by the database 40 in FIG. 15, the code region E3 is selected from among these as the one closest to the X coordinate (200) of the center 37a of the reading area 37.

In addition, since the code regions A4, C4, D4, and F4 are put into a database form as indicated by the database 41 in FIG. 16, the code region A4 is selected from among these as the one closest to the X coordinate (200) of the center 37a of the reading area 37.

The code regions B1, E2, E3, and A4 selected in S213 are set as the first to fourth code regions in S103. Step S213 of thus selecting the code regions set as the first to fourth code regions from among the code regions registered to the database corresponds to an example of the second information symbol selection step of the present invention.

Next, in S104 in FIG. 10, decoding processing of the selected B1, E2, E3, and A4 is carried out. After this, error correction is performed in S105 in FIG. 10, and if there is no error, the flow is ended normally (S106 in FIG. 10). This step S104 corresponds to an example of an information acquisition step.

However, if an error occurs in S105 in FIG. 10, the steps of S108, S109, S110, and S111 in FIG. 10 are performed one time via S107 in FIG. 10, and reselection processing of B1, E2, E3, and A4 selected as above is performed. In S107, it is determined whether or not an area flag has been set, which is done when reselection processing is performed in S107.

Reselection Processing

Figure 12:
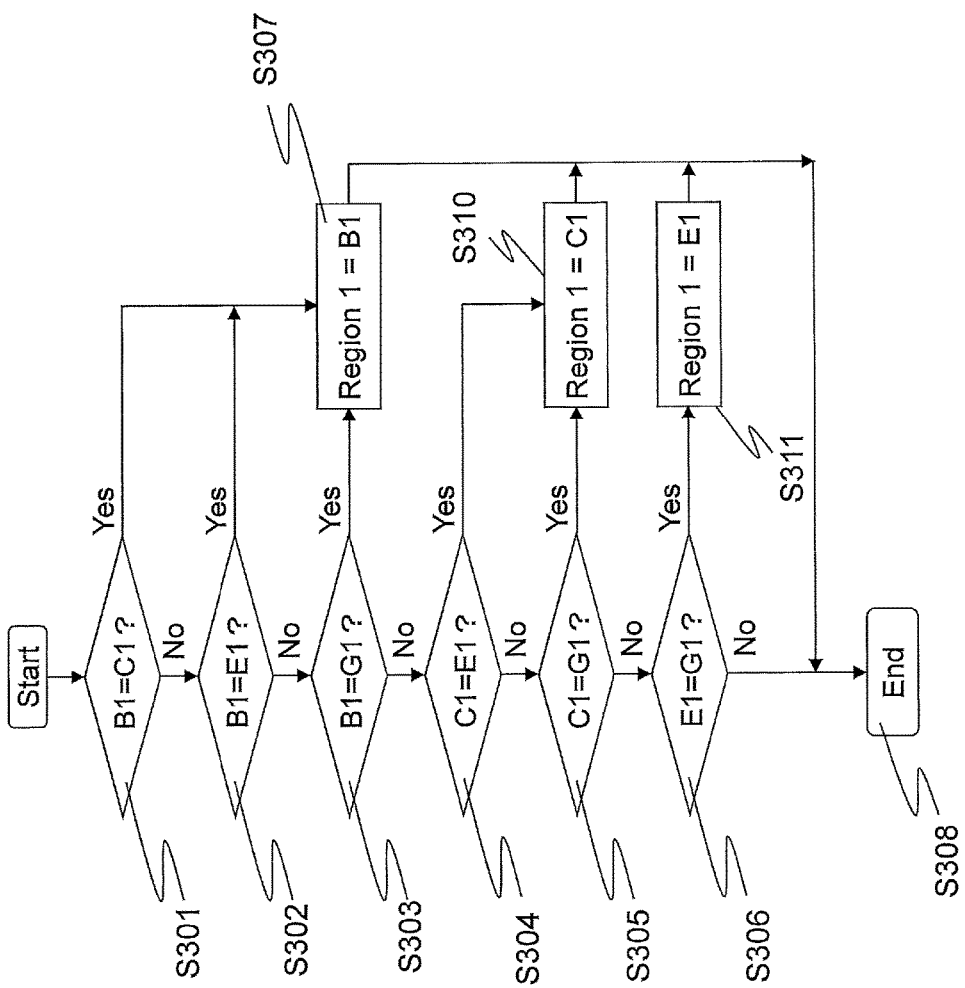
FIG. 12 is an operation flowchart of the information reading device in Embodiment 2 pertaining to the present invention.

In S108 in FIG. 10, for example, the selected code region B1 is examined as shown in FIG. 12, and compared with the code region C1 that is close to the X coordinate (200) of the center in the reading area 37 in FIG. 13 (S301 in FIG. 12). If the information of B1 and C1 matches, B1 is considered correct as the first code region from the left (S307 in FIG. 12). The confirmation of the code region 1 is completed in S308 in FIG. 12.

Next, the second code region 2 is confirmed in S109 in FIG. 10, then the third code region 3 is confirmed in S110 in FIG. 10, and then the fourth code region 4 is confirmed in S111 in FIG. 10. Once the confirmation of the code regions 1 to 4 is finished, the area flag is changed to 1 (AREA_FLG1=1) in S112 in FIG. 10.

The control processing then returns to S104 in FIG. 10, and error correction is performed again in S104 and S105 in FIG. 10. As a result, if there is an error, the control processing proceeds to S107 in FIG. 10, but since this is the second time, it moves to S113 in FIG. 10, and the processing ends abnormally.

If B1≠C1 in S301 in FIG. 12, then B1 is compared with E1, which is the next closest to the center 37a after C1, in S302 in FIG. 12. If B1=E1, the control processing moves from S307 to S308 in FIG. 12.

However, if B1≠E1 in S302 in FIG. 12, then B1 is compared with G1, which is the next closest to the center 37a after E1, in S303 in FIG. 12. If B1=G1, the control processing moves from S307 to S308 in FIG. 12.

However, if B1≠G1 in S303 in FIG. 12, what is being examined is changed from B1 to C1 in S304 in FIG. 12. More specifically, in S304 in FIG. 12, C1 is compared with E1, which is the next closest to the center 37a. If C1=E1, then the code region 1 is set to C1 in S310 in FIG. 12, and the control processing moves to the above-mentioned S308 in FIG. 12.

In S304 in FIG. 12, if C1≠E1, then C1 is compared with G1, which is the next closest to the center 37a, in S305 in FIG. 12. If C1=G1, the code region 1 is set to C1 in S310 in FIG. 12, and the control processing moves to the above-mentioned S308 in FIG. 12.

However, if C1≠G1 in S305 in FIG. 12, what is being examined is changed from C1 to E1 in S306 in FIG. 12. More specifically, in S306 in FIG. 12, E1 is compared with G1, which is the next closest to the center 37a, and if E1=G1, the code region 1 is set to E1 in S311 in FIG. 12, and the control processing moves to the above-mentioned S308 in FIG. 12.

In S306, if E1≠G1, then the reselection processing is ended in S308.

The same processing as the selection processing for this data region 1 is executed as the selection of the code region 2 in S109 in FIG. 10, and is executed as the selection of the code region 3 in S110 in FIG. 10, and is also executed as the selection of the code region 4 in S111 in FIG. 10.

Action and Effect

As discussed above, in this embodiment the information symbol is divided up, so that the code region located closer to the light receiving element of the information reading device (closer to the reading center) is selected and the information read from there, which allows more accurate information to be read. Specifically, the information symbol 18 selected in Embodiment 1 was indicated by c in FIG. 6B, but the region near the right end of c has a large curvature. In contrast, in Embodiment 2 here, the region near the right end of the information symbol 18 (the code region 4) is used using the code region A4, so the information can be read in a state that is closer to being planar.

Also, to describe a case when there is no edge line 34 through reference to FIG. 9B, since the code end position of the code region F2 is detected after the start mark 36f of the code region E4 is detected, a code region that integrates the code region E4 and the code region F2 with missing information may end up being determined to be valid as the fourth code region, and be subjected to decoding.

However, if the edge line 34 is provided and detected as in this embodiment, the code regions E4 and F2 will not be registered to the database, and will therefore not be subjected to decoding, so the information can be read properly.

Also, if reselection processing is performed when an error is discovered, the user does not need to remount the pharmaceutical syringe 10, rotate the pharmaceutical syringe, or the like, which means that less burden is imposed on the user.

Also, even in reselection processing when an error is discovered, more accurate reading can be achieved by selecting the code region located closest to the center.

Embodiment 3

Figure 18:
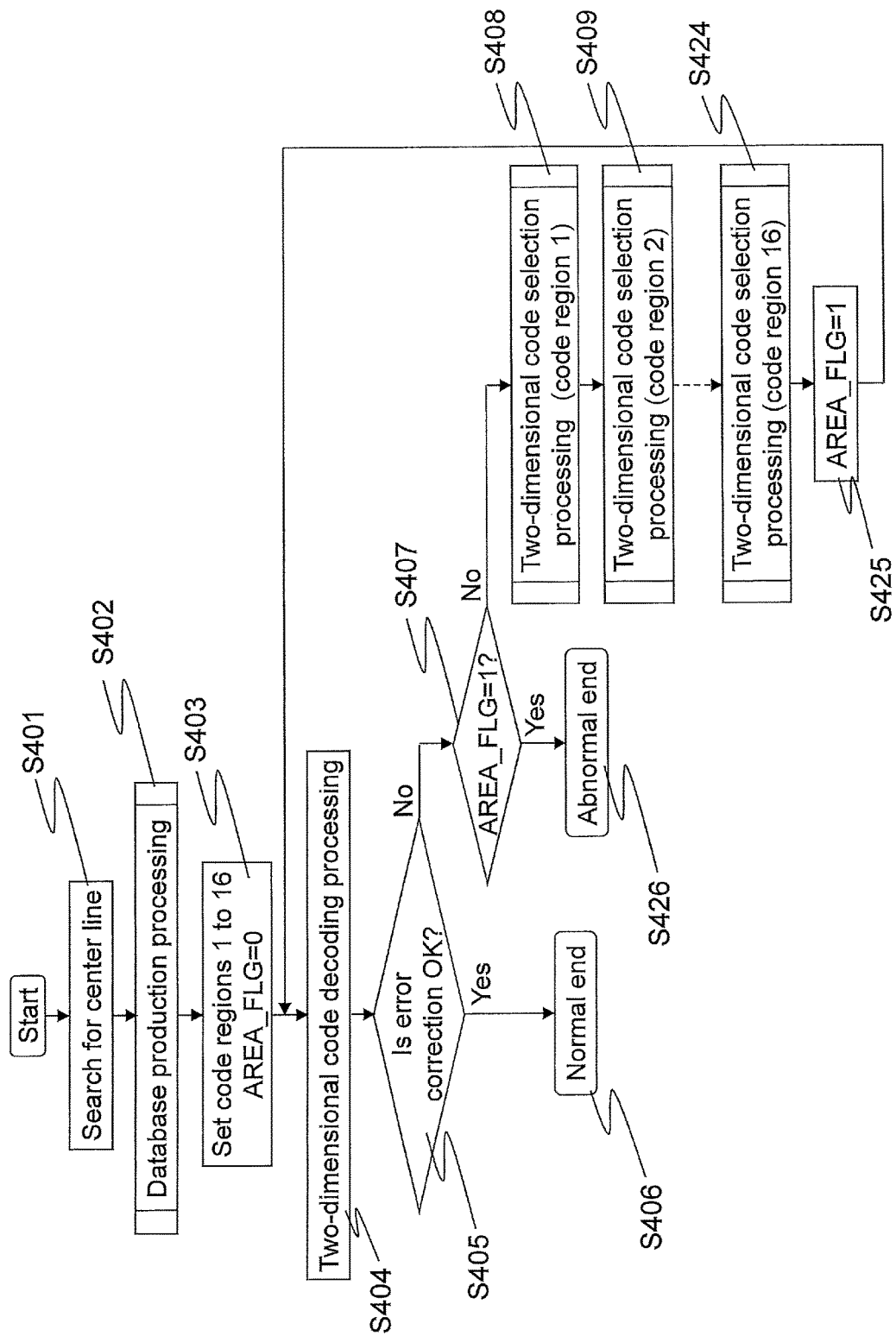
FIG. 18 is an operation flowchart of the information reading device in Embodiment 3 pertaining to the present invention.

FIGS. 17A, 17B and 18 illustrate Embodiment 3 of the present invention. In this embodiment, the information symbols 18 are divided into 16 code regions. To make the following description easier to understand, the information symbols 18 present in the reading area 37 are displayed as A (A1, A2, A3, A4, A5, A6, A7, A8, A9, A10, A11, A12, A13, A14, A15, and A16), B (B1, B2, B3, B4, B5, B6, B7, B8, B9, B10, B11, B12, B13, B14, B15, and B16), C (C1, C2, C3, C4, C5, C6, C7, C8, C9, C10, C11, C12, C13, C14, C15, and C16), D (D1, D2, D3, D4, D5, D6, D7, D8, D9, D10, D11, D12, D13, D14, D15, and D16), E (E1, E2, E3, E4, E5, E6, E7, E8, E9, E10, E11, E12, E13, E14, E15, and E16), F (F1, F2, F3, F4, F5, F6, F7, F8, F9, F10, F11, F12, F13, F14, F15, and F16), and G (G1, G2, G3, G4, G5, G6, G7, G8, G9, G10, G11, G12, G13, G14, G15, and G16).

That is, in Embodiment 3, as shown in FIG. 17, the information symbol 18 is divided in 16 horizontally and vertically, and the above-mentioned A to G information symbols 18 divided in 16 (A1 to A16, B1 to B16, C1 to C16, D1 to D16, E1 to E16, F1 to F16, and G1 to G16) are suitably spread out in this area divided in 16. Accordingly, to read the information in an information symbol 18, the code regions (1 to 16) divided in 16 must be selected as shown in FIG. 17b, in any combination of the A to G information symbols 18.

As shown in FIG. 17, the information recording medium 17 here is the same as that in Embodiments 1 and 2 above in that the sheet-form member 33 is in the form of a strip. As shown in FIG. 17b, when this slender sheet-form member 33 is affixed to the pharmaceutical syringe 10, one end of the sheet-form member 33 overlaps the other end, so that the edge line 34 overlaps part of the information symbol 18.

Since each information symbol 18 is divided in 16, A2, A3, A4, B1, C1, C2, C3, C4, A6, A7, A8, B5, C5, C6, C7, C8, A10, A11, A12, B9, C9, C10, C11, C12, A14, A15, A16, B13, C13, C14, C15, and C16 are in the top row. D4, E1, E2, E3, F3, F4, G1, G2, D8, E5, E6, E7, F7, F8, G5, G6, D12, E9, E10, E11, F11, F12, G9, G10, D16, E13, E14, E15, F15, F16, G13, and G14 are in the bottom row.

When the information symbol 18 is thus divided in 16, the start marks 36 (36b, 36c, 36d, 36e, and 36f) only indicate a section in the longitudinal direction of the sheet-form member 33 in the top and bottom areas.

In FIG. 17, information is read from the information symbol 18 closest to the center in the reading area 37. In Embodiment 3, however, since the information symbol 18 is divided in 16, B1 is elected as the first code region (A1 to G1), and then E2 is selected as the second code region (A2 to G2).

E3 is selected as the third code region (A3 to G3), and A4 is selected as the fourth code region (A4 to G4).

B5 is selected as the fifth code region (A5 to G5), and E6 is selected as the sixth code region (A6 to G6).

E7 is selected as the seventh code region (A7 to G7), and A8 is selected as the eighth code region (A8 to G8).

B9 is selected as the ninth code region (A9 to G9), and E10 is selected as the tenth code region (A10 to G10).

E11 is selected as the eleventh code region (A11 to G11), and A12 is selected as the twelfth code region (A12 to G12).

B13 is selected as the thirteenth code region (A13 to G13), and E14 is selected as the fourteenth code region (A14 to G14).

E15 is selected as the fifteenth code region (A15 to G15), and A16 is selected as the sixteenth code region (A16 to G16).

These are integrated to read the information symbol 18 (the 16 areas 1 to 16).

The details of the reading operation here are substantially the same as in Embodiment 2, and therefore will not be described again.

FIG. 18 is a flowchart of the operation of the information reading device in Embodiment 3 pertaining to the present invention. As shown in FIG. 18, step S401 (the same as S101) is executed, and database production processing is performed in S402. The selection of code regions corresponding to the code regions 1 to 16 divided in 16 is performed here.

The description here will contrast with Embodiment 2. In Embodiment 2, first the code region A2 is registered to the database as valid data, but in Embodiment 3, the code regions A2, A6, A10, and A14 are registered to the database together. Then, the code regions A3, A7, A11, and A15 are similarly registered to the database together. Then, the code regions A4, A8, A12, and A16 are similarly registered to the database together. Then, the code regions B1, B5, B9, and B13 are registered to the database together. Then, successively, the code regions C1, C5, C9, and C13 are registered to the database together, the code regions C2, C6, C10, and C14 are registered to the database together, the code regions C3, C7, C11, and C15 are registered to the database together, and the code regions C4, C8, C12, and C16 are registered to the database together.

Then, in the bottom row, the code regions D4, D8, D12, and D16 are registered to the database together, the code regions E1, E5, E9, and E13 are registered to the database together, the code regions E2, E6, E10, and E14 are registered to the database together, and the code regions E3, E7, E11, and E15 are registered to the database together. Then, straddling the edge line 34, the code regions F3, F7, F11, and F15 are registered to the database together, and the code regions F4, F8, F12, and F16 are registered to the database together. Following this, the code regions G1, G5, G9, and G13 are registered to the database together, and the code regions G2, G6, G10, and G14 are registered to the database together.

Then, the code regions set to the code regions 1 to 16 are selected from among the code regions registered to the database. This selection may be performed in the units of four code regions registered to the database together, or may be performed for every code region divided in 16, but the results will be the same regardless of the selection method. This selection involves selecting the coordinate closest to the reading center, so the coordinate in a direction perpendicular to the reading direction does not affect the selection result. In addition to the condition of selecting the coordinate closest to the reading center, a condition of selecting the code region at the coordinate closest to the center line 35 may be included. In this case, the selection must be performed for every code region divided in 16.

The code regions thus selected are set as the code regions 1 to 16 in S403.

Then, two-dimensional decoding processing is performed in S404, error correction is performed in S405, and if there is no error, the processing is ended normally in S406. The coordinate of each code region in a direction perpendicular to the center line 35 is preset, and the code regions are decoded according to this setting.

If an error occurs in S405, it is determined in S407 whether or not reselection processing has already been performed once. More specifically, it is determined whether or not an area flag has been set, which is done when reselection processing is performed.

The reselection processing of the code regions 1 to 16 is performed in S408 to S424. This reselection processing of the code regions is performed one by one on the code regions divided in 16. This reselection processing is the same as in Embodiment 2, so it will not be described again.

In Embodiment 3, because the information symbol 18 is also divided in a direction perpendicular to the center line 35 (the reading direction), even if part of the information symbol 18 is soiled and difficult to read, for example, just that portion can be changed to another code by reselection processing, so reading performance can be improved.

Specifically, in Embodiment 3, since the divisions are finer than in Embodiment 2, reselection can be performed on smaller regions during reselection processing, so there is less effect of dirt or smudges.

Figure 19:
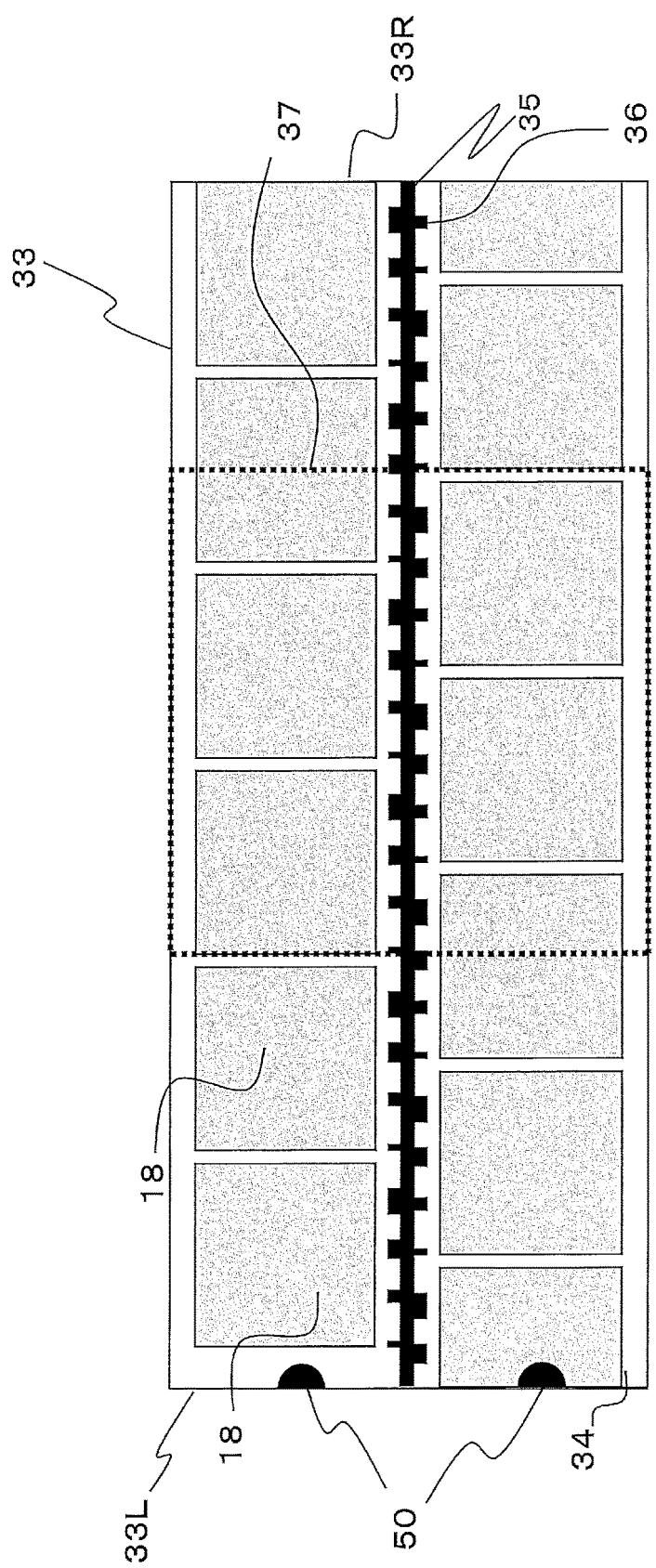
FIG. 19 is a plan view of the information recording medium in a modification example of an embodiment pertaining to the present invention.

In Embodiments 1 to 3 above, the edge line 34, which ran perpendicular to the longitudinal direction, was provided to one end and/or the other end in the longitudinal direction of the slender sheet-form member 33. This edge line 34 corresponds to an example of an end recognition component, but this edge line 34 does not need to be specially provided, as long as one end and/or the other end in the longitudinal direction of the slender sheet-form member 33 will form a shadow, for example, so that a pseudo-edge line 34 can be detected in reading by the light emitting element 31 and the light receiving element 32. Nor does this need to be formed as a line, and instead a circle, a square, a semicircle, or some other mark may be provided. FIG. 19 shows the information recording medium 17 in which a semicircular mark 50 is formed at the left end 33L of the sheet-form member 33. In any case, it is important that the end recognition component be able to detect one or both ends in the longitudinal direction of the sheet-form member 33, and it is acceptable if just one end can be detected. Being able to detect this end is a characteristic of the edge line 34, which is an example of the end recognition component.

Also, the longitudinal direction of the sheet-form member 33 described in Embodiments 1 to 3 above corresponds to an example of the reading direction of a reading device, but the sheet-form member 33 need not be in the form of a strip, and the short-side direction may be used instead if the shape is one that is taller than it is wide. In other words, an end recognition component for making recognize the information reading device the end of the sheet-form member should be provided at one or both ends of the sheet-form member.

Also, in Embodiments 1 to 3 above, a plurality of information symbols 18 were disposed on both sides of the center line 35, but a plurality of information symbols 18 may be disposed in the longitudinal direction of the slender sheet-form member 33. In this case, the center line 35 will be provided on the upper or lower edge side of the plurality of information symbols 18 that are arranged in the longitudinal direction.

Furthermore, in Embodiments 1 to 3 above, the strip-form information recording medium 17 was affixed to the outer peripheral face of the pharmaceutical syringe 10, which was in the form of a columnar body, but if the outer peripheral face of the pharmaceutical syringe 10 is integrally covered with a cover, then the strip-form information recording medium 17 may be affixed to the outer peripheral face of this cover.

Also, in Embodiments 1 to 3 above, the pharmaceutical syringe main body 100 was given as an example of a columnar main body to which an information recording medium is affixed, but a pharmaceutical syringe is not the only option. For example, the above-mentioned information recording medium may be affixed to a test tube or the like for holding a blood sample, a chemical sample, or another such sample. Furthermore, the columnar main body is not limited to a container that holds something, and may be the finished product itself. Specifically, an information recording medium on which a product identification number, a lot number, or other such information is recorded may be wound around the product itself. Nor is the columnar body limited to having a cylindrical shape on the outside, and may instead be in the form of a quadrangular prism, a hexagonal prism, or the like.

Also, in Embodiments 1 to 3 above, it was described that one end overlapped the other end when the information recording medium 17 was affixed to the pharmaceutical syringe main body 100, but depending on the length of the information recording medium in the reading direction, it is also possible that one end or the other will overlap the middle of the sheet-form member 33. In other words, the sheet-form member 33 should be wound around the pharmaceutical syringe main body 100 so that one end (such as the left end 33L) or the other end (such as the right end 33R) overlaps the surface 33a.

Also, in Embodiments 1 to 3 above, if there were a plurality of information symbols selected in the first information symbol selection step, then the information symbol closest to the center 37a of the reading area 37 was selected in the second information symbol selection step, but if there is just one information symbol selected in the first information symbol selection step, the second information symbol selection step need not be performed. Also, if one information symbol is selected in the first information symbol selection step, then even if there is an information symbol that can be registered, the first information symbol selection step may be ended and the selected information symbol decoded.

In other words, what is important is that an information symbol 18 that is cut off at the end of the sheet-form member 33 or that overlaps the end of the sheet-form member 33 not be selected, and that an information symbol 18 that is not cut off at the end of the sheet-form member 33 and does not overlap the end of the sheet-form member 33 be selected.

Also, in Embodiment 2 above, when there were a plurality of regions selected as information regions in the first information symbol selection step, the region (code region) closest to the center 37a of the reading area 37 was selected in the second information symbol selection step, but if just one region (code region) is selected in the first information symbol selection step, the second information symbol selection step need not be performed. Also, if one region (code region) is selected as a specific information region of the information symbol in the first information selection step, then even if there is another region that can be registered, the first information symbol selection step may be ended, and the second information region selection step need not be performed. In other words, what is important is that an information region (code region) that is cut off at the end of the sheet-form member 33 or that overlaps the end of the sheet-form member 33 not be selected, and that an information region (code region) that is not cut off at the end of the sheet-form member 33 and does not overlap the end of the sheet-form member 33 be selected.

Also, in above Embodiments, if the information symbol 18 or the region of the information symbol was to the right of the center 37a of the reading area 37, the distance from the center 37a was the distance between the center 37a and the position of the start mark of the information symbol 18 or the region of the information symbol, and if the information symbol 18 or the region of the information symbol was to the left of the center 37a, the distance from the center 37a was the distance between the center 37a and the position of the right end of the information symbol or the region of the information symbol (the end on the opposite side from the start mark). However, this is not the only option. The distance from the center 37a may be determined on the basis of the center portion of the information symbol or the region of the information symbol. For instance, when C1 and E1 are compared in FIG. 13A, the distance between the center position of C1 and the center 37a is found by (238+38/2)−200, or S7. Meanwhile, the center position of E1 is found by 200−(76+38/2), or 105. It can thus be concluded that C1 is closer than E1 to the center 37a.

Also, a flag indicating whether or not the reselection processing shown in FIG. 12 ended normally may be set for each of the code regions divided in four. For example, if E1 # G1 in S306, processing is performed to set up a flag for an abnormal end, and if an abnormal flag is set up, control processing may be performed so that there is a move not from S108 to S109 in FIG. 10, but to S113.

Some or all of the steps, processing, procedure, and so forth in the information reading method in the above embodiments may be accomplished using a program, for example. Also, some or all of the steps, processing, procedure, and so forth in the information reading method in Embodiments 1 to 3 above may be carried out by a central processing unit (CPU). The above-mentioned program operates in conjunction with a computer.

As a utilization mode of the above-mentioned program, for example, it may be recorded to a ROM or other such recording medium that can be read by a computer. As another utilization mode of the program, it may be transmitted through the Internet or another such transmission medium, or through light, radio waves, or another such transmission medium, and read by a computer. For instance, the pharmaceutical injection device in the above embodiments may be connected by USB, etc., to a computer, and a program for executing the above-mentioned information reading method may be transmitted through the Internet. This computer is not limited to a CPU or other such hardware, and may be firmware or an OS. Also, some or all of the steps, processing, procedure, and so forth in the information reading method in the embodiments may be realized by hardware, or by software. Combined processing of software and hardware may also be used.

INDUSTRIAL APPLICABILITY

The information recording medium, columnar body, information reading device, and pharmaceutical injection device of the present invention have the effect of allowing an information symbol to be properly read, and are expected to find wide application as pharmaceutical injection devices and so forth used in hospitals and at home.

The invention claimed is:

1. An information reading method comprising:
   obtaining reading information from an information recording medium including a sheet-form member, a plurality of information symbols displayed on a surface of the sheet-form member, and an end recognition component;
   a first information symbol selection step including selecting information symbols that do not overlap the end of the sheet-form member and are not cut off at the end of the sheet-form member, and ignoring any information symbols that overlap an end of the sheet-form member or are cut off at an end of the sheet-form member; and
   an information acquisition step including validating reading information read from the selected information symbols;
   wherein the information recording medium is affixed to an outer peripheral face of a columnar body,
   each of the information symbols include the same information,
   the end recognition component is provided on at least one end of the sheet-form member, the end recognition component configured to allow an information reading device able to read the information symbols to recognize the end of the sheet-form member; and
   the information recording medium is wound around the columnar main body such that a portion of the information recording medium overlaps itself.

2. The information reading method according to claim 1, further comprising:
   a second information symbol selection step including further selecting the information symbol disposed closest to a light receiving element if there are a plurality of information symbols selected in the first information symbol selection step, the light receiving element provided at the information reading device and configured to receive light reflected from the information recording medium; and
   the information reading step further includes validating reading information from the information symbol selected in the second information symbol selection step.

3. A non-transitory computer readable medium comprising:
   a program for causing a computer to execute the first information symbol selection step and the information acquisition step in the information reading method according to claim 1.

4. An information reading method comprising:
   obtaining reading information from an information recording medium including a sheet-form member, a plurality of information symbols displayed on a surface of the sheer-form member, and an end recognition component;
   a first information region selection step including selecting a region of a plurality of information symbols that do not overlap the end of the sheet-form member and are not cut off at the end of the sheet-form member as an information region, and ignoring a region of the information symbols that overlap the end of the sheet-form member or are cut off at the end of the sheet-form member; and
   an information acquisition step including validating reading information from the information symbols obtained by combining the information regions selected in the first information region selection step;
   wherein the information recording medium is affixed to an outer peripheral face of a columnar body,
   each of the information symbols include the same information, and are divided into a plurality of regions along a reading direction of an information reading device, the information reading device able to read the information symbols,
   the end recognition component is provided on at least one end of the sheet-form member, the end recognition component configured to allow the information reading device to recognize the end of the sheet-form member; and
   the information recording medium is wound around the columnar main body such that a portion of the information recording medium overlaps itself.

5. The information reading method according to claim 4, further comprising:
   a second information region selection step including selecting the information region disposed closest to a light receiving element, when there are a plurality of information regions selected in the first information region selection step, the light receiving element provided at the information reading device for receiving light reflected from the information recording medium; and
   the information acquisition step further includes validating reading information from the information symbols obtained by combining the information region selected in the second information region selection step.

6. A non-transitory computer readable medium comprising:
   a program for causing a computer to execute the first information region selection step and the information acquisition step in the information reading method according to claim 4.

* * * * *